(12) United States Patent
Phan et al.

(10) Patent No.: US 11,066,534 B2
(45) Date of Patent: Jul. 20, 2021

(54) POLYETHER-MODIFIED SILICONE COMPOSITION, SURFACTANT, FOAM STABILIZER, POLYURETHANE FOAM FORMING COMPOSITION, AND COSMETIC PREPARATION INCLUDING SAID COMPOSITION, AND METHOD FOR PRODUCING SAID COMPOSITION

(71) Applicant: DOW TORAY CO., LTD., Tokyo (JP)

(72) Inventors: Son Thanh Phan, Ichihara (JP); Seiki Tamura, Ichihara (JP); Hiroyuki Inagaki, Ichihara (JP); Ikutaro Morikawa, Ichihara (JP)

(73) Assignee: DOW TORAY CO., LTD., Tokyo (JP)

( * ) Notice: Subject to any disclaimer, the term of this patent is extended or adjusted under 35 U.S.C. 154(b) by 93 days.

(21) Appl. No.: 16/342,679

(22) PCT Filed: Oct. 6, 2017

(86) PCT No.: PCT/JP2017/036428
§ 371 (c)(1),
(2) Date: Apr. 17, 2019

(87) PCT Pub. No.: WO2018/074257
PCT Pub. Date: Apr. 26, 2018

(65) Prior Publication Data
US 2020/0048427 A1 Feb. 13, 2020

(30) Foreign Application Priority Data
Oct. 18, 2016 (JP) .............................. JP2016-204536

(51) Int. Cl.
*C08K 5/06* (2006.01)
*C08G 77/46* (2006.01)
*A61K 8/894* (2006.01)
*C08J 9/00* (2006.01)
*C08L 83/12* (2006.01)

(52) U.S. Cl.
CPC ................ *C08K 5/06* (2013.01); *A61K 8/894* (2013.01); *C08J 9/0042* (2013.01); *C08G 77/46* (2013.01); *C08J 2205/06* (2013.01); *C08J 2205/10* (2013.01); *C08J 2375/04* (2013.01); *C08J 2375/08* (2013.01); *C08L 83/12* (2013.01)

(58) Field of Classification Search
CPC ......... C08K 5/06; C08J 2375/04; C08G 77/46
See application file for complete search history.

(56) References Cited

U.S. PATENT DOCUMENTS

| | | |
|---|---|---|
| 3,249,550 A | 5/1966 | Metters |
| 3,507,815 A | 4/1970 | Bailey et al. |
| 3,629,308 A | 12/1971 | Bailey et al. |
| 4,122,029 A | 10/1978 | Gee et al. |
| 4,147,874 A * | 4/1979 | Beschke .............. C07D 213/12 546/251 |
| 4,520,160 A | 5/1985 | Brown |
| 4,857,583 A | 8/1989 | Austin et al. |
| 4,936,917 A | 6/1990 | Harakal et al. |
| 5,153,293 A | 10/1992 | Hales et al. |
| 5,430,097 A | 7/1995 | Petroff et al. |
| 5,527,855 A | 6/1996 | Petroff et al. |
| 5,648,444 A | 7/1997 | Austin et al. |
| 5,691,392 A * | 11/1997 | Okoroafor ............. C08J 9/0023 521/112 |
| 5,844,010 A | 12/1998 | Burkhart et al. |
| 5,869,727 A | 2/1999 | Crane et al. |
| 5,883,142 A * | 3/1999 | Chojnacki .............. C08G 77/46 521/112 |
| 6,071,977 A | 6/2000 | Austin et al. |
| 6,162,888 A | 12/2000 | Lee et al. |
| 6,417,258 B1 | 7/2002 | Aoki et al. |
| 6,506,810 B2 | 1/2003 | Borgogelli et al. |
| 7,947,124 B2 * | 5/2011 | Moss ..................... C09D 11/36 106/31.27 |
| 8,034,848 B2 | 10/2011 | Landers et al. |
| 8,912,277 B2 | 12/2014 | Glos |
| 2004/0029986 A1 | 2/2004 | Ghobary et al. |
| 2005/0070618 A1* | 3/2005 | Miller ................ C08G 18/4883 521/112 |
| 2009/0069457 A1 | 3/2009 | Brown et al. |
| 2012/0101175 A1 | 4/2012 | Willoughby et al. |
| 2012/0245305 A1 | 9/2012 | Souda et al. |
| 2012/0269875 A1 | 10/2012 | Tamura et al. |
| 2013/0065028 A1 | 3/2013 | Fujii et al. |
| 2013/0281593 A1* | 10/2013 | Yamazaki ............ C09D 11/322 524/377 |
| 2015/0080480 A1 | 3/2015 | Tamura et al. |
| 2017/0267879 A1* | 9/2017 | Kohzuki ................ C09D 11/10 |

FOREIGN PATENT DOCUMENTS

| | | |
|---|---|---|
| CN | 103317783 A | 9/2013 |
| CN | 104592829 A | 5/2015 |
| CN | 104592840 A | 5/2015 |
| EP | 3572470 A1 | 11/2019 |
| GB | 955916 A | 4/1964 |

(Continued)

OTHER PUBLICATIONS

English translation of International Search Report for PCT/JP2017/036428 dated Dec. 26, 2017, 3 pages.

(Continued)

*Primary Examiner* — Marc S Zimmer
(74) *Attorney, Agent, or Firm* — Warner Norcross + Judd LLP

(57) ABSTRACT

Provided is a polyether-modified silicone composition. The composition comprises (A) a polyether-modified silicone, and (B) a monool organic compound. The monool organic compound (B) is selected from (B1) a glycol ether compound having a hydrogen atom substituted by an alkyl group having from 2 to 8 carbon atoms at one end, a secondary alcoholic hydroxy group at the other end, from 2 to 3 repeating oxyalkylene units having from 2 to 4 carbon atoms, and (B2) a tripropylene glycol monomethyl ether. Isopropyl alcohol does not exceed 1 mass % of the entire composition. Applications and manufacturing methods for the composition are also provided.

7 Claims, No Drawings

(56) References Cited

FOREIGN PATENT DOCUMENTS

| | | |
|---|---|---|
| GB | 1149744 A | 4/1969 |
| JP | H05179293 A | 7/1993 |
| JP | H06271803 A | 9/1994 |
| JP | H07216089 A | 8/1995 |
| JP | H08156143 A | 6/1996 |
| JP | H11116670 A | 4/1999 |
| JP | H11504379 A | 4/1999 |
| JP | 2000327785 A | 11/2000 |
| JP | 2002137234 A | 5/2002 |
| JP | 2003077910 A | 3/2003 |
| JP | 2004352918 A | 12/2004 |
| JP | 2005187985 A | 7/2005 |
| JP | 2005534770 A | 11/2005 |
| JP | 2007186557 A | 7/2007 |
| JP | 2009265425 A | 11/2009 |
| JP | 2010195870 A | 9/2010 |
| JP | 2010247532 A | 11/2010 |
| JP | 2010535931 A | 11/2010 |
| JP | 2010539280 A | 12/2010 |
| JP | 2011116902 A | 6/2011 |
| JP | 2012082273 A | 4/2012 |
| JP | 2012246397 A | 12/2012 |
| JP | 2013076062 A | 4/2013 |
| JP | 2013151658 A | 8/2013 |
| WO | 2007127004 A1 | 11/2007 |
| WO | 2011049248 A1 | 4/2011 |
| WO | 2016166979 A1 | 10/2016 |

OTHER PUBLICATIONS

Machine assisted English translation of JPH05179293A obtained from https://patents.google.com on Jul. 12, 2019, 5 pages.
Machine assisted English translation of JPH06271803A obtained from https://patents.google.com on Jul. 12, 2019, 5 pages.
Machine assisted English translation of JP2003077910A obtained from https://patents.google.com on Jul. 12, 2019, 6 pages.
Machine assisted English translation of JP2004352918A obtained from https://patents.google.com on Jul. 12, 2019, 6 pages.
Machine assisted English translation of JP2005187985A obtained from https://patents.google.com on Jul. 12, 2019, 8 pages.
Machine assisted English translation of CN103317783A obtained from https://patents.google.com on Jul. 12, 2019, 9 pages.
Machine assisted English translation of CN104592829A obtained from https://patents.google.com on Jul. 12, 2019, 7 pages.
Machine assisted English translation of WO2016166979A1 obtained from https://patents.google.com on Jul. 12, 2019, 32 pages.
Machine assisted English translation of CN104592840A obtained from https://patents.google.com on Jul. 17, 2019, 9 pages.
Machine assisted English translation of JPH08156143A, obtained from patents.google.com on Apr. 12, 2021, 7 pages.
Machine assisted English translation of JP2002137234A, obtained from patents.google.com on Apr. 12, 2021, 10 pages.
Machine assisted English translation of JP2007186557A , obtained from patents.google.com on Apr. 12, 2021, 9 pages.
Machine assisted English translation of JP2009265425A, obtained from patents.google.com on Apr. 12, 2021, 7 pages.
Machine assisted English translation of JP2010195870A, obtained from patents.google.com on Apr. 12, 2021, 10 pages.
Machine assisted English translation of JP2010247532A, obtained from patents.google.com on Apr. 12, 2021, 11 pages.
Machine assisted English translation of JP2012082273A, obtained from patents.google.com on Apr. 12, 2021, 9 pages.
Machine assisted English translation of JP2012246397A, obtained from patents.google.com on Apr. 12, 2021, 7 pages.

* cited by examiner

POLYETHER-MODIFIED SILICONE COMPOSITION, SURFACTANT, FOAM STABILIZER, POLYURETHANE FOAM FORMING COMPOSITION, AND COSMETIC PREPARATION INCLUDING SAID COMPOSITION, AND METHOD FOR PRODUCING SAID COMPOSITION

CROSS-REFERENCE TO RELATED APPLICATIONS

This application is the National Stage of International Application No. PCT/JP2017/036428 filed on 6 Oct. 2017, which claims priority to and all advantages of Japanese Patent Appl. No. 2016-204536 filed on 18 Oct. 2016, the content of which is hereby incorporated by reference.

TECHNICAL FIELD

The present invention relates to a novel polyether-modified silicone composition comprising (A) a polyether-modified silicone having a specific structure, and (B) a specific glycol ether compound that is liquid at 5° C., that has a secondary alcoholic hydroxy group and does not contain a heteroatom other than oxygen in the molecule, and that does not contain isopropyl alcohol (IPA) in an amount exceeding 1 mass % of the entire composition; and to a manufacturing method for this composition. The present invention also relates to a surfactant, foam stabilizer (including the functions of a foam control agent, same below), cosmetic raw material, and cosmetic containing this composition. The present invention also relates to a polyurethane form-forming composition containing this composition and to a polyurethane foam obtained therefrom.

BACKGROUND ART

Because polyether-modified silicones enable surfactant activity, compatibility with blowing agents, and affinity with urethane foam systems to be controlled based on the EO % and size of the polyether portion, the introduction of a hydroxyl group or hydrophobic group to the silicone terminal portion, and modification with two or more different polyether groups so as to be able to design the average molecular weight, they are useful as surfactants for foaming control and foaming stability in all polyurethane foam formulations, such as rigid foams, semi-rigid foams, high resilience (HR) foams, flexible foams, and microcellular foams. However, polyether modified silicones tend to form and thicken hydrogels in the presence of water, which sometimes limits their usefulness. For example, raw material compositions used to obtain polyurethane foams usually contain components other than an isocyanate {such as polyols, water, catalyst, and sometimes a surfactant, etc.}. The storage stability of the so-called premix solution is poor, and industrially, it is sometimes difficult to keep the solution in a homogeneous state for long periods of time. Similar problems related to the interaction between and compatibility of components require special handling during industrial production and sale (distribution) of some components in the form of preblend systems. Therefore, there is demand for dispersion solvents and preparation methods that allow polyether-modified silicone compositions to be used stably in a homogeneous state.

Patent Document 1 and Patent Document 2 report non-hydrolyzable polyether modified silicones produced by a hydrosilylation reaction between a SiH group-containing organopolysiloxane and a polyether containing an allyl group on one end, and production methods for polyurethane foams using these silicones as cell stabilizers or surfactants. Patent Document 1 discloses an example in which the hydrosilylation is carried out in a xylene or toluene solvent, and Patent Document 2 discloses an example in which hydrosilylation is carried out in a mixed solvent of IPA and toluene. Patent Document 3 discloses an example in which the hydrosilylation of a SiH group-containing organopolysiloxane and a polyether containing an allyl group on one end is carried out in an IPA solvent. Because these highly volatile organic solvents are hazardous and highly flammable, they are stripped out of the polyether-modified silicone product system by applying heat or under reduced pressure conditions.

However, the polyether-modified silicone has excellent cell stability when the organic solvent has been removed by vacuum stripping after hydrosilylation in a common organic solvent. The air bubbles generated by the stirring become fine and very stable, preventing the bursting of bubbles. As a result, the space at the top of the reactor quickly fills with bubbles, and the pressure reduction operation must be performed very slowly and gradually. In other words, this production method is disadvantageous from the standpoint of mass production.

In order to solve this problem, Patent Document 4 has proposed a method in which the polyether-modified silicone is produced in a liquid high boiling point polyol solvent such as dipropylene glycol (DPG) and in which the polyol solvent remains in the product system. However, because DPG does not have good affinity to SiH group-containing organopolysiloxanes, the hydrosilylation is slow especially in the case of polysiloxane with a large degree of polymerization. As a result, side reactions such as dehydrogenation reactions and acetal formation tend to occur.

Patent Document 5 proposes a method in which a polyether-modified silicone is produced by hydrosilylation in a liquid saturated higher alcohol solvent such as isostearyl alcohol (ISA) and in which the higher alcohol remains in the product system. It has also been reported that these polyether-modified silicone compositions are useful as surfactants for flexible polyurethane foams. Patent Document 6 discloses a production method for flexible polyurethane foam in which a mixture of a commercially available polyether-modified silicone product and a branched alcohol such as isostearyl alcohol is used as a foam stabilizer, and in which foaming occurs in the presence of water. It has been reported that a fine, defect-free cell structure is obtained due to the effect of the branched alcohol.

However, because these higher alcohols comprise a large percentage of the alkyl groups in the molecule and are very lipophilic, they are not sufficiently compatible with the polyol constituting the main component in the polyurethane foam-forming composition. Also, because polyether-modified silicones used as cell stabilizers for rigid polyurethane foams generally usually have a better hydrophile-lipophile balance (HLB) than those for flexible foams, higher alcohols are not compatible with very hydrophilic polyether-modified silicones, and it is difficult combine them (as they are unsuitable as diluents and act as a foam-breaker in foam formulations).

Patent Document 7 proposes a method in which a polyether modified silicone is produced by hydrosilylation in an alkanediol monocarboxylic acid ester solvent such as 2,2,4-trimethyl-1,3-pentanediol monoisobutyrate (Texanol) and in which the solvent remains in the product system. It has been reported that polyether-modified silicone surfactants obtained in this manner improve the quality or performance of flexible, rigid, and high resilience (HR) polyurethane foams. Because Texanol has greater molecular polarity and a larger number of methyl branches than isostearyl alcohol, it is compatible with the other components and compatible with a larger number of polyols and polyether-modified silicones.

However, when a polyether-modified silicone has extremely hydrophilic polyethylene glycol (PEG) homopolymer chains, compatibility with Texanol is insufficient in the low temperature environment of winter, and coagulation and separation of the surfactant and cloudiness becomes difficult to stop. Handling problems such as reheating, stirring and dissolution remain unsolved. Also, according to Patent Document 9 introduced in the next paragraph, because it contains volatile components, Texanol causes fogging of glass when used in automotive interior trim foam.

Patent Document 8 discloses a method for producing polyether-modified silicone by hydrosilylation in a hydroxyl group-free ester oil, and a composition obtained in this manner. It has been reported that this composition contributes to uniformity of cell structure when used as a surfactant for flexible polyurethane foams. Patent Document 9 discloses a process for producing a polyether-modified silicone by hydrosilylation in a high boiling point natural vegetable oil and a composition obtained in this manner. It has been reported that this composition contributes to uniformity of cell size and compression set reduction when used as a surfactant for high resilience (HR) polyurethane foams.

However, many of the ester oils tested in Patent Document 8 have a freezing point higher than 0° C., and solidification of the ester oil, and thus the surfactant, is likely to occur in the winter. Also, ester oils with long-chain alkyl groups tend to have poor compatibility with polyether-modified silicones. When the polyether-modified silicone has a large molecular weight, once solidified, phase separation is likely to occur during heating and melting, and the solution may not return to a uniform state even after stirring.

While the vegetable oils tested in Patent Document 9 have a lower freezing point than the aforementioned ester oils, the vegetable oils have a triglyceride backbone as the basic molecular structure and there are usually three ester groups per molecule. Because, as a result, the molecular weight of these vegetable oils is as much as two or three times greater than that of ordinary ester oils and their compatibility with polyether-modified silicone is generally poor, use of the polyether-modified silicone tested in Patent Document 9 is limited to low molecular weight (low polymerization degree) HR polyurethane foams (for interior use such as in automotive seats).

In addition to these restrictions, when a high boiling point non-reactive solvent such as an ester oil, vegetable oil, or long-chain alkyl benzene is included in a surfactant for a polyurethane foam, the non-reactive solvent remains in the urethane foam and may migrate (leach) from the final product. As a result, they are unsuitable for use as a solvent.

Patent Document 10 discloses a composition obtained by mixing together a polyether-modified silicone and cashew nut shell oil or a derivative thereof, use of the composition as a foam stabilizer for polyurethane foam, and a foam obtained in this manner.

However, cashew nut shell oil is a complex mixture of long-chain alkenyl phenol derivatives including anacardic acid, cardanol, and cardol, and has a plurality of phenolic hydroxyl groups and carboxyl groups in each molecule that have higher acidity than alcoholic hydroxyl groups. As a result, it is difficult to use as a reaction solvent in polyether-modified silicone production. In addition, the long-chain alkenyl phenol derivative and polyether-modified silicone may not be very compatible due to very different molecular structures. Also, use of cashew nut shell oil and derivatives thereof is limited because of their strong color.

As mentioned above, the surfactants and cell stabilizer applications proposed in Patent Documents 1 to 10 are insufficient as solvents for polyether-modified silicones, inappropriate in industrial production and applications, insufficiently versatile technologically, or are unable to realize sufficient foam performance. Component (B) in the invention of the present application has neither been mentioned nor suggested in these documents.

Patent Document 11 and Patent Document 12 disclose non-hydrolyzable polyether-modified silicones and their use as cell stabilizers, and methods for producing flexible polyurethane foams using the same. Patent Document 11 and Patent Document 12 disclose a large number of solvents, and disclose that a solvent represented by $RO(C_3H_6O)_xH$ can be used to suppress gelation during silicone production. However, the technical effects of realizing a uniform polyether-modified silicone composition (solution) using these solvents compared to realizing a polyether-modified silicone composition (solution) using other solvents are not specifically disclosed, and remains simply the disclosure of a single non-limiting example of a solvent that could be selected. In addition, many of the listed solvents are not practical because they inhibit the reaction and cause heterogeneity and gelation in the reaction system when used in silicone production. In order to find the optimum solvent, a person skilled in the art would have to conduct extensive research to verify the reactivity and stability of each solvent, because the patent documents do not specifically mention how a suitable solvent would be selected. Therefore, Patent Document 11 and Patent Document 12 do not clearly teach a person skilled in the art about polyether-modified silicone compositions using a solvent selected as a dispersion medium for the polyether-modified silicone or the technical advantages of doing so.

Patent Document 13 also proposes a composition obtained by producing a polyether-modified silicone by hydrosilylation in a phenyl ether solvent such as ethylene glycol phenyl ether (PhEG) or propylene glycol phenyl ether (PhPG) and leaving the solvent in the product system. These solvents improve the transparency and lower the freezing point of polyether-modified silicone-containing compositions serving as surfactants in urethane foam formulations without sacrificing other properties of the surfactants. It has also been reported that polyether-modified silicone surfactants having the high degree of polymerization of siloxane prepared using 20 mass % PhEG perform the same in flexible polyurethane foam formulations compared to a control sample (identical in terms of the design structure of the modified silicone) prepared by hydrosilylation in an IPA solvent followed by solvent removal. Note that when calculated based on the description of the examples in this document, the chemical structure of the polyether-modified silicone is $MD_{226}D^*{}_{13}D^{**}{}_{17}M\{*=C_3H_6O(EO)_{12}-COCH_3, **=C_3H_6O(EO)_{18}(PO)_{18}-COCH_3\}$. It is believed that the reaction was carried out by adding a 1.6× molar excess of both allyl polyethers per SiH group to be consumed.

However, because phenyl ether solvents are generally expensive, use of these surfactants is economically disadvantageous in most polyurethane foam markets which demand low costs. Also, because the phenyl ether solvent has a somewhat high viscosity, the improvement to the fluidity of the polyether-modified silicone by dilution is less dramatic.

In Patent Document 13, production of polyether-modified silicones having the same design structure is also possible in propylene glycol monobutyl ether (BuPG) and dipropylene glycol monomethyl ether (MeDPG). However, it has been reported that cloudiness, aggregation, and separation gradually occur when these compositions are left standing at low temperatures. Those skilled in the art would have a difficult time conceiving of compositions using these dispersions.

Patent Document 14 relates to a method for producing a polyether-modified silicone by hydrosilylation, and includes the production of a polyether-modified silicone by a continuous hydrosilylation reaction process. Various organic solvents that can be used in the hydrosilylation reaction process are listed in the text, and several glycol ethers are mentioned. While the document mentions that the hydrosilylation solvent can be removed in a subsequent step (paragraph 0023 on page 7, paragraph 0024 on page 8), it neither mentions nor suggests using (B) a specific glycol ether compound that is liquid at 5° C. and that has a secondary alcoholic hydroxy group but no heteroatom other than oxygen in the molecule as the solvent for the polyether-modified silicone. It also neither mentions nor suggests leaving the solvent in the modified-silicone product system or the advantages of doing so.

Patent Document 15 relates to a glass cleaning composition having antifogging properties, and discloses a composition comprising: a') a water-soluble $C_{10}$-$C_{16}$ alkyl sulfate: 0.3 to 5 mass %; b') a compound selected from monomethyl or monoethyl ether of diethylene glycol or dipropylene glycol: 1 to 5 mass %; c') isopropyl alcohol (IPA): 5 to 15 mass %; d') water: 93.7 to 75 mass %; and e') polyether-modified silicone: 0.001 to 2 mass %. Specifically, the document only discloses compositions in which IPA and water are added in excess or in great excess relative to the polyether-modified silicone in component b'), and a large amount of IPA and water are essential to this application. In other words, compounds containing a polyether-modified silicone and a specific glycol ether compound but less than 1 mass % IPA and the benefits of these compounds are neither described nor suggested.

Patent Document 16 relates to a low viscosity cell stabilizer aqueous solution for flexible thermosetting polyurethane foam, the aqueous solution comprising: a") polyether modified silicone: 40 to 70 mass %; b") organic surfactant: 0.5 to 20 mass %; c") Water: 10 mass % or more; and d") organic solvent additive: 0 mass % or more. In this document, component d") is a solvent selected from a group consisting of dipropylene glycol, butyl diglycol, ethylene glycol, diethylene glycol, propylene glycol, phthalate, polyether, animal and vegetable oils, mineral oils and/or liquid-form antifreezes. Preferred examples of these antifreezes include low molecular weight monools or diols such as ethanol, isopropanol, dipropylene glycol, ethylene glycol, and butyl diglycol. Here, butyl diglycol is a trade name or abbreviation of diethylene glycol monobutyl ether (BuDEG).

In Patent Document 16, this merely amounts to the disclosure of many examples of non-limiting solvents. There is no specific teaching or suggestion of compositions in which a polyether-modified silicone and a specific glycol ether compound are selectively used as the dispersion medium or the technical effects of these compositions. Also, the aforementioned composition is an aqueous solution, and an organic solvent is only added as an optional component.

The document only discloses the invention of an aqueous solution based on the technical idea that it differs from a composition in which a polyether-modified silicone has been dispersed in a specific glycol ether compound.

As mentioned above, Patent Documents 11 to 16 neither clearly disclose nor suggest compositions using a polyether-modified silicone and a specific glycol ether compound selected for use as the dispersion medium or the technical advantages of doing so. When the compositions disclosed primarily in these documents are used specifically as surfactants and foam stabilizers for urethane foams, they are insufficient in terms of performance, versatility, quality, safety, environmental friendliness, and production costs. The compositions disclosed in these documents may also be technically and economically disadvantageous when used in these applications. Therefore, there is demand for the development of novel compositions containing polyether-modified silicones which have stable quality and performance characteristics, and which have sufficient utility when used in applications such as surfactants and foam stabilizers.

PRIOR ART DOCUMENTS

Patent Document 1: GB 955916 A
Patent Document 2: GB 1149744 A
Patent Document 3: U.S. Pat. No. 4,122,029 A (JP S54-024959 A1)
Patent Document 4: U.S. Pat. No. 4,857,583 A (JP S64-087633 A1)
Patent Document 5: U.S. Pat. No. 4,520,160 A (JP S60-156733 A1)
Patent Document 6: U.S. Pat. No. 6,506,810 A (JP 2002-167418 A)
Patent Document 7: U.S. Pat. No. 5,153,293 A (JP H05-125189 A)
Patent Document 8: U.S. Pat. No. 5,648,444 A (JP H11-504379 A)
Patent Document 9: U.S. Pat. No. 6,071,977 A (JP H10-279688 A)
Patent Document 10: U.S. Pat. No. 8,912,277 A (JP 2011-512428 A)
Patent Document 11: U.S. Pat. No. 3,629,308 A
Patent Document 12: U.S. Pat. No. 3,507,815 A
Patent Document 13: U.S. Pat. No. 5,430,097 A (JP H07-216089 A)
Patent Document 14: WO 2007/127004 A1
Patent Document 15: U.S. Pat. No. 3,249,550 A
Patent Document 16: U.S. Pat. No. 8,034,848 A (JP 2010-501031 A)

SUMMARY OF THE INVENTION

Problem to be Solved by the Invention

It is an object of the present invention to solve the aforementioned problems by providing a polyether-modified silicone composition that can be produced industrially and supplied in large quantities at low cost, that is very safe and environmentally friendly, and that has excellent quality in terms of mixing stability, handling and workability, and storage stability in compositions containing a dispersion medium, and that can be used in applications such as surfactants and foam stabilizers. It is also an object of the present invention to provide a surfactant and foam stabilizer containing this polyether-modified silicone composition.

Similarly, it is an object of the present invention to provide a cosmetic raw material and cosmetic containing this composition.

It is another object of the present invention to provide a polyurethane foam-forming composition containing this polyether-modified silicone composition and a polyurethane foam prepared using this.

It is another object of the present invention to provide a method for manufacturing a polyether-modified silicone composition that can be supplied in large quantities to the market at low cost, that is user-friendly and environmentally friendly, and that has excellent quality.

While attempting to solve these problems, the present inventors discovered a new problem with polyurethane foam-forming compositions and polyurethane foams prepared using these compositions. Specifically, there is growing market demand for polyurethane foams with "low emission" properties. (In the present specification, polyurethane foam will sometimes be referred to as "urethane foam" or simply "foam".) This means components such as chemical substances generated by or volatilized from polyurethane foams have been quantitatively reduced. Specifically, in order to reduce volatile components generated by the foam (=low volatile organic compounds or low VOC) and prevent sick building syndrome and allergies, demand has been expressed for a reduction in chemical substances released from the foam over time (=low emission chemical compounds) and make the adhesion of components volatilized from foam used in car interiors from adhering to window glass less likely to occur (=low fogging). Aside from differences in the types and properties of chemical substances, this essentially means reducing the release of components derived from foam.

It is another object of the present invention to provide a polyurethane foam-forming composition that satisfies these low emission requirements and a polyurethane foam prepared using this composition.

Means for Solving the Problem

As a result of conducting extensive research to solve these problems, the present inventors discovered that the problems could be solved using a polyether-modified silicone composition comprising component (A) and component (B) below and no more than 1 mass % isopropyl alcohol (IPA) relative to the entire composition. The present invention is a product of this discovery.

(A) 1 type or 2 or more types of polyether-modified silicone represented by Formula (1):

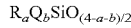
$R_aQ_bSiO_{(4-a-b)/2}$

{where each R independently represents a monovalent hydrocarbon group having 1 to 30 carbon atoms and no aliphatic unsaturated bond or a silicon atom-containing organic group, each Q independently represents a polyoxyalkylene-containing organic group represented by the formula: —$C_xH_{2x}$O—$(C_2H_4O)_{t1}(C_3H_6O)_{t2}(C_4H_8O)_{t3}$—Y (where x, t1, t2 and t3 are numbers satisfying 2≤x≤8, 0≤t1≤60, 0≤t2≤50, 0≤t3≤50, 2≤t1+t2+t3≤110, and Y is selected from among a hydrogen atom, alkyl groups having from 1 to 4 carbon atoms, and a $COCH_3$ group), and a and b are numbers in the ranges 1.0≤a≤2.5 and 0.0001≤b≤1.5, respectively}, (B) 1 type or 2 or more types of a monool organic composition selected from (B1) or (B2) and characterized by being a liquid at 5° C. and having one secondary alcoholic hydroxyl group but no heteroatom other than oxygen in the molecule:

(B1) a glycol ether compound having a hydrogen atom substituted by an alkyl group having from 2 to 8 carbon atoms at one end, a secondary alcoholic hydroxy group at the other end, and from 2 to 3 repeating oxyalkylene units having from 2 to 4 carbon atoms, (B2) a tripropylene glycol monomethyl ether.

The present inventors also discovered that the aforementioned problems could be solved by a surfactant, foam stabilizer, polyurethane foam-forming composition, cosmetic raw material, or cosmetic containing this composition. The present invention is also a product of this discovery as well. In addition, they discovered that these problems could be solved by a polyurethane foam obtained from this polyurethane foam-forming composition. The present invention is a product of this discovery as well.

In addition, the present inventors discovered that the aforementioned problems could be solved by a method for manufacturing a polyether-modified silicone composition comprising at least a step selected from among initiating or promoting a hydrosilylation reaction between an organic hydrogen polysiloxane and a polyether compound having an alkenyl group at one end of the molecular chain (1) substantially solvent free,
(2) in the presence of a monool organic compound serving as component (B), or
(3) in the presence of a volatile organic solvent (B') other than component (B). In the case of (1) or (3), solvent exchange is conducted with the monool organic compound serving as component (B). The present invention is also a product of this discovery. In addition, they discovered that these problems could be solved by a manufacturing method comprising a continuous hydrosilylation process. The present invention is a product of this discovery as well.

Specifically, the object of the present invention can be achieved by the following.

[1] A polyether-modified silicone composition comprising component (A) and component (B) below, and isopropyl alcohol (IPA) does not exceed 1 mass % of the entire composition.

(A) 1 type or 2 or more types of polyether-modified silicone represented by Formula (1):

$R_aQ_bSiO_{(4-a-b)/2}$

{where each R independently represents a monovalent hydrocarbon group having 1 to 30 carbon atoms and no aliphatic unsaturated bond or a silicon atom-containing organic group, each Q independently represents a polyoxyalkylene-containing organic group represented by the formula: —$C_xH_{2x}$O—$(C_2H_4O)_{t1}(C_3H_6O)_{t2}(C_4H_8O)_{t3}$—Y (where x, t1, t2 and t3 are numbers satisfying 2≤x≤8, 0≤t1≤60, 0≤t2≤50, 0≤t3≤50, 2≤t1+t2+t3≤110, and Y is selected from among a hydrogen atom, alkyl groups having from 1 to 4 carbon atoms, and a $COCH_3$ group), and a and b are numbers in the ranges 1.0≤a≤2.5 and 0.0001≤b≤1.5, respectively}, (B) 1 type or 2 or more types of a monool organic composition selected from (B1) or (B2) and characterized by being a liquid at 5° C. and having one secondary alcoholic hydroxyl group but no heteroatom other than oxygen in the molecule:

(B1) a glycol ether compound having a hydrogen atom substituted by an alkyl group having from 2 to 8 carbon atoms at one end, a secondary alcoholic hydroxy group at the other end, and from 2 to 3 repeating oxyalkylene units having from 2 to 4 carbon atoms, (B2) a tripropylene glycol monomethyl ether.

The object of the present invention can be advantageously achieved by the following.

[2] A polyether-modified silicone composition according to [1], wherein component (A) is a linear polyether-modified silicone represented by Formula (1') below.

[Formula 1]

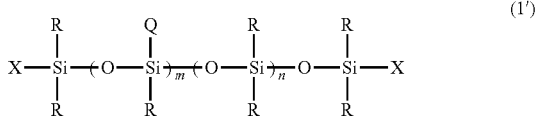
(1')

{where R and Q are defined in the same manner as above, X is R or Q, n is a number from 0 to 1000, and m is a number in a range from 0 to 200, provided at least one X is Q when m=0}

[3] A polyether-modified silicone composition according to [2], wherein n and m in Formula (1') are numbers in the range 25≤m+n≤230.

[4] A polyether-modified silicone composition according to any one of [1] to [3], wherein the functional group Q in Formula (1) or Formula (1') is a polyoxyalkylene group-containing organic group excluding a polyoxyethylene group-containing organic group represented by the formula: $-C_xH_{2x}O-(C_2H_4O)_{t1}-Y$ {where 2≤x≤8, 10≤t1≤60, and Y is selected from a hydrogen atom, alkyl groups having from 1 to 4 carbon atoms, and a $COCH_3$ group}.

[4-1] A polyether-modified silicone composition according to any one of [1] to [3], wherein the functional group Q represented by the formula: $-C_xH_{2x}O-(C_2H_4O)_{t1}(C_3H_6O)_{t2}(C_4H_8O)_{t3}-Y$ in Formula (1) or Formula (1') is preferably a polyoxyalkylene group-containing organic group in which 1<t2≤50 and whose essential component is a polypropylene unit represented by $C_3H_6O$.

[5] A polyether-modified silicone composition according to any one of [1] to [4], wherein component (B) is one type or two or more types of monool organic compound selected from a group consisting of dipropylene glycol monobutyl ether, tripropylene glycol monobutyl ether, dipropylene glycol mono (iso) propyl ether, tripropylene glycol mono (iso) propyl ether, dipropylene glycol monoethyl ether, tripropylene glycol monoethyl ether, and tripropylene glycol monomethyl ether.

[6] A polyether-modified silicone composition according to any one of [1] to [5], wherein component (B) is one type or two or more types of distilled and refined monool organic compound.

[7] A polyether-modified silicone composition according to any one of [1] to [6], wherein the mass ratio of component (A) and component (B) is in a range from 20/80 to 96/4.

[7-1] A polyether-modified silicone composition according to any one of [1] to [6], wherein the mass ratio of component (A) and component (B) is in a range from 33/67 to 88/12.

[8] A polyether-modified silicone composition according to any one of [1] to [7], wherein the functional group Q in Formula (1) or Formula (1') is a polyoxyalkylene group-containing organic group represented by the formula: $-C_xH_{2x}O-(C_2H_4O)_{t1}(C_3H_6O)_{t2}(C_4H_8O)_{t3}-Y$, where x, t1, t2 and t3 are numbers satisfying 2≤x≤8, 0≤t1≤60, 1≤t2≤50, 0≤t3≤50, and 6≤t1+t2+t3≤50, and Y is selected from a hydrogen atom, alkyl groups having from 1 to 4 carbon atoms, and a $COCH_3$ group.

[8-1] A polyether-modified silicone composition according to any one of [1] to [8], further comprising (C) at least one type of polyalkylene glycol or derivative thereof being a liquid at 25° C., having at least one terminal hydroxyl group substitutable by a hydrocarbon group having from 1 to 8 carbon atoms selected from alkyl, aralkyl and aryl groups, and having from 4 to 50 repeating oxyalkylene units having from 2 to 4 carbon atoms in an amount from 0 to 300 parts by mass per 100 parts by mass component (A) and component (B), the viscosity of the entire composition at 25° C. being in a range from 10 to 30,000 mm²/s.

The object of the present invention can also be achieved by the following compositions.

[9] A surfactant comprising a polyether-modified silicone composition according to any one of [1] to [8].

[10] A foam stabilizer comprising a polyether-modified silicone composition according to any one of [1] to [8].

[11] A polyurethane foam-forming composition comprising a polyether-modified silicone composition according to any one of [1] to [8].

[12] A polyurethane foam-forming composition comprising:

(a) a polyol;

(b) a polyisocyanate;

(c) a catalyst;

(d) a foam stabilizer containing a polyether-modified silicone composition according to any one of claims 1 to 8; and (e) optionally at least one additional component selected from a group consisting of a foam stabilizer other than component (d), a blowing agent, a diluent, a chain extender, a crosslinker, water, a non-aqueous blowing agent, a filler, a strengthening agent, a pigment, a dye, a colorant, a flame retardant, an antioxidant, an anti-ozone agent, an ultraviolet light stabilizer, an antistatic agent, a fungicide, and an antimicrobial agent.

[13] A polyurethane foam-forming composition according to [11] or [12], comprising from 0.3 to 8.0 parts by mass (A) polyether-modified silicone in a polyether-modified silicone composition according to any one of [1] to [8] per 100 parts by mass (a) polyol.

[14] A polyurethane foam obtained from a polyurethane foam-forming composition according to any one of [11] to [13].

[15] A polyurethane foam according to [14], wherein the foam is a rigid foam, semi-rigid foam, high-resilience (HR) foam, flexible foam, or microcellular foam, and has low emission properties.

[16] A cosmetic raw material comprising a polyether-modified silicone composition according to any one of [1] to [8].

[17] A cosmetic comprising a polyether-modified silicone composition according to any one of [1] to [8].

The object of the present invention can also be achieved advantageously by the following manufacturing methods.

[18] A method for manufacturing a polyether-modified silicone composition according to any one of [1] to [8], the method comprising at least the steps of:

(I) initiating a substantially solvent-free hydrosilylation reaction between an organic hydrogen polysiloxane and a polyether compound having an alkenyl group at one end of the molecular chain; and (II) diluting or accelerating the reaction by adding the monool organic compound serving 30 as component (B).

[19] A method for manufacturing a polyether-modified silicone composition according to any one of [1] to [8], the method comprising at least the step (I') of: initiating or promoting a hydrosilylation reaction between an organic hydrogen polysiloxane and a polyether compound having an alkenyl group at one end of the molecular chain in the presence of the monool organic compound serving as component (B).

[20] A method for manufacturing a polyether-modified silicone composition according to any one of [1] to [8], the method comprising at least the steps of:

(I'') initiating or promoting a hydrosilylation reaction between an organic hydrogen polysiloxane and a polyether compound having an alkenyl group at one end of the molecular chain in the presence of a volatile organic solvent (B') different from component (B); and (II') conducting solvent exchange of the volatile organic solvent (B') with the monool organic compound serving as component (B).

[21] A method for manufacturing a polyether-modified silicone composition according to any one of [18] to [20], wherein the hydrosilylation reaction between the organic hydrogen polysiloxane and the polyether compound having an alkenyl group at one end of the molecular chain is performed in a continuous hydrosilylation process.

Effect of the Invention

The present invention is able to provide a polyether-modified silicone composition that can be produced industrially and supplied in large quantities at low cost, that is very safe and environmentally friendly, and that has excellent quality in terms of mixing stability, handling and workability, and storage stability in compositions containing a dispersion medium, and that can be used in applications such as surfactants and foam stabilizers. It can also provide a surfactant and foam stabilizer containing this composition. Similarly, it can provide a cosmetic raw material and cosmetic containing this composition.

The present invention is able to provide a polyurethane foam-forming composition containing this polyether-modified silicone composition and a polyurethane foam prepared using this.

The present invention is able to provide a method for manufacturing a polyether-modified silicone composition that can be supplied in large quantities to the market at low cost, that is user-friendly and environmentally friendly, and that has excellent quality. This comprehensively resolves the performance problems of polyether-modified silicone compositions, production problems directly linked to industrial costs, and application problems that have been difficult to resolve and overcome in the past. This makes it possible for novel polyether-modified silicone compositions to be introduced more widely in the market, and to be used more fully as a high-performance raw material.

EMBODIMENT OF THE INVENTION

The following is a more detailed description of a polyether-modified silicone composition of the present invention. The composition of the present invention contains (A) 1 type or 2 or more types of polyether-modified silicone, and (B) a specific monool organic compound as a dispersion medium for this silicone. The component (A)/component (B) mass ratio in the composition is preferably from 20/80 to 96/4 and more preferably from 33/67 to 88/12. This composition may optionally contain other components. Each component will be described first.

[(A) Component]

Component (A) is the main component in a composition of the present invention and is one type or two or more types of polyether-modified silicone represented by Formula (1) below.

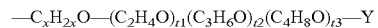

Formula (1):

In Formula (1), each R independently represents a monovalent hydrocarbon group having 1 to 30 carbon atoms and no aliphatic unsaturated bond or a silicon atom-containing organic group, and each Q independently represents a polyoxyalkylene-containing organic group represented by the following formula:

$-C_xH_{2x}O-(C_2H_4O)_{t1}(C_3H_6O)_{t2}(C_4H_8O)_{t3}-Y$

Here, x, t1, t2 and t3 are numbers satisfying $2 \le x \le 8$, $0 \le t1 \le 60$, $0 \le t2 \le 50$, $0 \le t3 \le 50$, $2 \le t1+t2+t3 \le 110$, and Y is selected from among a hydrogen atom, alkyl groups having from 1 to 4 carbon atoms, and a $COCH_3$ group.

In Formula (1), a and b are numbers in the ranges $1.0 \le a \le 2.5$ and $0.0001 \le b \le 1.5$, respectively. As long as it is within these ranges, the structure of component (A) may take the form of any linear, branched, cyclic, or reticulated siloxane bond, but is preferably a linear polyether-modified silicone when used as a surfactant, foam stabilizer, polyurethane foam-forming composition, cosmetic raw material, or cosmetic.

A preferred example of component (A) in the present application is a linear polyether-modified silicone represented by Formula (1') below:

[Formula 2]

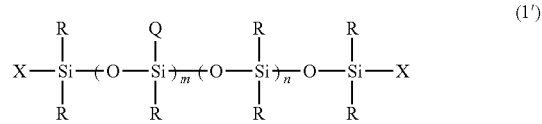

In Formula (1'), R and Q are defined in the same manner as above, X is R or Q, n is a number from 0 to 1000, and m is a number in a range from 0 to 200. At least one X is Q when m=0. In other words, component (A) has a polysiloxane side chain and a polyoxyalkylene group-containing organic group represented by Q on one or both ends.

In Formula (1) or Formula (1'), each R independently represents a monovalent hydrocarbon group having 1 to 30 carbon atoms and no aliphatic unsaturated bond or a silicon atom-containing organic group, and preferably independently represents an alkyl group or allyl group having from 1 to 10 carbon atoms. Examples include a linear, branched or cyclic alkyl group, such as a methyl, ethyl, n-propyl, i-propyl, n-butyl, i-butyl, s-butyl, pentyl, neopentyl, cyclopentyl or hexyl, or a phenyl group. A methyl group or phenyl group for R is especially preferred from an industrial standpoint.

At least some R groups may be a long-chain alkyl group having from 8 to 20 carbon atoms, a cycloalkyl group such as a cyclohexyl group, or an aryl group such as tolyl, xylyl or naphthyl.

Similarly, some R groups may be a silicon atom-containing organic group having a carbosiloxane dendrimer structure or a silicon atom-containing organic group having a linear siloxane structure (siloxane macromonomer). Preferred examples of these functional groups include the silicon atom-containing organic groups disclosed as functional group L1 in JP 2013-151658 A.

A methyl group or phenyl group for R is especially preferred from an industrial standpoint, but use of a long-chain alkyl group or silicon atom-containing organic group for some of these groups in a cosmetic may improve the affinity or emulsification performance with other raw materials and improve the feel.

Q is a polyoxyalkylene-containing organic group bonded to a silicon atom and is defined by the formula: —$C_xH_{2x}$O—$(C_2H_4O)_{t1}(C_3H_6O)_{t2}(C_4H_8O)_{t3}$—Y. Here, x is the number of carbon atoms in an alkylene group bonding with silicon atoms and satisfies $2 \le x \le 8$, preferably $2 \le x \le 6$ when the same functional group is derived from the alkenyl group. Y is an end group with a polyoxyalkylene structure, and is selected from among a hydrogen atom, alkyl groups having from 1 to 4 carbon atoms, and a $COCH_3$ group. Y is preferably a hydrogen atom or methyl group from the standpoint of usability in a foam stabilizer and the safety and stability of the modified silicone. In Formula (1) or Formula (1'), the Q groups may be two or more different types of polyoxyalkylene group-containing organic group in the same molecule.

t1, t2, and t3 represent the number of oxyethylene units, oxypropylene units, and oxybutylene units constituting the polyoxyalkylene structure, and are numbers satisfying $2 \le t1+t2+t3 \le 110$, preferably $6 \le t1+t2+t3 \le 50$, and more preferably $8 \le t1+t2+t3 \le 40$. t1, t2, and t3 are each $0 \le t1 \le 60$, $0 \le t2 \le 50$, and $0 \le t3 \le 50$. For the reason described below, $1 \le t2 \le 50$ is preferred.

In the present invention, compatibility with component (B) may decrease if Q consists only of oxyethylene units, so having an oxypropylene unit or an oxybutylene unit is preferred. At least one Q group is preferably an oxypropylene unit. In the formula, $1 \le t2 \le 50$ is preferred, and $8 \le t1+t2+t3 \le 40$ and $5 \le t2 \le 30$ is especially preferred.

In the present invention, from the standpoint of compatibility with component (B), polyoxyalkylene group-containing organic groups not preferred as Q are functional groups represented by the formula: —$C_xH_{2x}$O—$(C_2H_4O)_{t1}$—Y {where $2 \le x \le 8$, $10 \le t1 \le 60$, and Y is selected from a hydrogen atom, alkyl groups having from 1 to 4 carbon atoms, and a $COCH_3$ group} which only have a polyoxyethylene structure excluding a linked alkylene group ($C_xH_{2x}$) and end group Y. It is preferably a polyoxyalkylene group-containing organic group excluding these functional groups.

In an alkylene group bonded to a silicon atom, the alkylene moiety has three or more carbon atoms and constitutes an oxypropylene unit or oxybutylene unit. This may be a linear alkylene group or a branched isoalkylene group such as an isopropylene group or isobutylene group.

In Formula (1'), n and m are the degree of siloxane polymerization in the linear polyether-modified silicone, n is a number from 0 to 1000, and m is a number in a range from 0 to 200. Preferably, n is a number in a range from 1 to 500 and m is a number in a range from 1 to 150. More preferably, n and m are numbers in the range $25 \le m+n \le 230$. Also, more preferably, $n > m$, $25 \le m+n \le 230$, and m is a number in a range from 1 to 50.

Because these preferred polyether-modified silicones have especially improved hydrophilicity and inevitably contain a certain number of oxypropylene units or oxybutylene units, compatibility is improved between the polyol and isocyanate main components of a polyurethane foam-forming composition and a foam stabilizer, increasing the number of possible applications due to improved stability of the premix solution, and having the desired foam control effect. The functions of a surfactant or foam stabilizer are improved and handling during and after synthesis is also improved.

These polyether-modified silicones can be obtained by hydrosilylation of a polyether compound having a carbon-carbon double bond such as an alkenyl group at one end of the molecular chain and an organic hydrogen polysiloxane in the presence or absence of a solvent. While the carbon-carbon double bond in the polyether compound and the Si—H in the organic hydrogen polysiloxane theoretically react at 1:1, both are not equal. Therefore, synthesis is preferably performed by adding a small amount of extra polyether component before the hydrosilylation reaction.

More preferably, the polyether-modified silicone serving as component (A) in the present invention is obtained from a hydrosilylation reaction with an organic hydrogen polysiloxane represented by Formula (1'H) below:

[Formula 3]

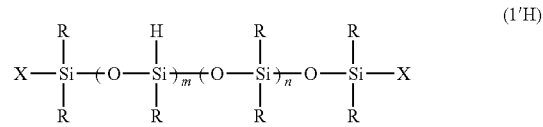

{where R is defined in the same manner as above, X is R or H, n and m are defined in the same manner as above, and at least one X is H when m=0}
and a polyether compound having an alkenyl group at one end of the molecular chain represented by Formula (2) below:

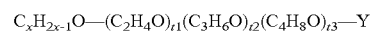

{where x, t1, t2 and t3 are the same numbers as above, Y is defined in the same manner as above, and $C_xH_{2x-1}$ is a linear or branched alkenyl group having a carbon-carbon double bond}.

[Component (B)]

Component (B), which is a characteristic component in a composition of the present invention, is one type or two or more types of monool organic composition selected from (B1) or (B2) and characterized by being a liquid at 5° C. and having one secondary alcoholic hydroxyl group but no heteroatom other than oxygen in the molecule. Compound (B) is a solvent for a polyether-modified silicone, and may be introduced to the composition as a solvent during the synthesis reaction or may be introduced to the composition in the form of solvent substitution or solvent addition to the system after a synthesis reaction for the polyether-modified silicone performed in the presence or absence of another solvent.

Component (B) is preferably a monool organic compound having a boiling point enabling distillation or purification by distillation, and is preferably a distilled or purified monool organic compound.

Component (B1) is a glycol ether compound having a hydrogen atom substituted by an alkyl group having from 2 to 8 carbon atoms at one end, a secondary alcoholic hydroxy group at the other end, and from 2 to 3 repeating oxyalkylene units having from 2 to 4 carbon atoms, and must have a relatively low degree of polymerization, be capped at one end with a hydrocarbon group, and have a secondary alcoholic hydroxyl group at the other end. Examples of these compounds include dipropylene glycol monobutyl ether, tripropylene glycol monobutyl ether, dipropylene glycol mono (iso) propyl ether, tripropylene glycol mono (iso) propyl ether, dipropylene glycol monoethyl ether, and tripropylene glycol monoethyl ether. An alcoholic hydroxyl group other than a secondary alcoholic hydroxyl group is not inappropriate because environmental compatibility and safety are poor and the technical effects of the present invention cannot be sufficiently achieved when a monool organic compound such as diethylene glycol monobutyl ether having a primary alcoholic hydroxyl group is used.

Component (B2) is a tripropylene glycol monomethyl ether, which is a monool organic compound in which the hydrogen atom at one end is substituted by a methyl group having one carbon atom. It does not fall under the definition for component (B1) but has the same technical effects as component (B1). Component (B2) is believed to have an affinity with polyether-modified silicones and environmental comparability similar to component (B1) because it has a tripropyleneoxy structure because of the effect of the end groups.

For component (B), component (B1) or component (B2) may be used alone or a mixture of both may be used. Any mixing ratio may be adopted, and a mixture of two or more types of component (B) may be used. However, when a monool organic compound is used that does not fall under component (B1) or component (B2), it sometimes does not function sufficiently as a reaction solvent or dispersion medium for the target polyether-modified silicone and the object of the present invention sometimes cannot be achieved. For example, the present inventors discovered in their research that when a hydrosilylation reaction is performed using as a solvent, for example, diethylene glycol monobutyl ether (BuDEG), which does not have a secondary alcoholic hydroxyl group, side reactions such as a dehydrogenation reaction and acetal formation readily occur if a trace amount of acidic impurities coexists in the reaction system due to fluctuations in the composition of raw material lots. Also, glycol ether compounds in which there is only one repeating oxyalkylene unit having from 2 to 4 carbon atoms have a low boiling point or flash point and are inferior from the standpoint of safety and environmental compatibility. Among these are compounds having a simple structure with two carbon atoms, known as cellosolves, which are highly toxic and which are regulated by various laws.

Component (B) functions as a solvent (dispersion medium) for component (A). In a composition of the present invention, the (A)/(B) mass ratio for these components is in the range of 20/80 to 96/4, which is important from the standpoint of the quality and performance of the composition, usefulness in applications, and handling. Preferably, the (A)/(B) mass ratio is in the range of 33/67 to 88/12. When the amount of component (B) in the composition is 20 mass % or more, preferably 25 mass % or more, the low-temperature stability of the entire composition is improved.

A polyether-modified silicone composition of the present invention containing component (A) and component (B) has a viscosity at 25° C. in a range from 10 to 30,000 mm$^2$/s, which is important from the standpoint of usefulness in applications and handling.

A polyether-modified silicone composition of the present invention may include dimethylpolysiloxane, organic modified silicones such as other polyether-modified silicones, silanes, and silicone resins in a range that does not impair the technical characteristics of the present invention. In this case, the content of any organosilicon compound other than component (A) is preferably in a range not exceeding the same amount of component (A) in terms of mass in the overall composition. A polyether-modified silicone composition of the present invention may be substantially free of other organosilicon compounds if functioning as a foam stabilizer or surfactant.

[Component (C)]

A polyether-modified silicone composition of the present invention may optionally include (C) at least one type of polyalkylene glycol or derivative thereof being a liquid at 25° C., having at least one terminal hydroxyl group substitutable by a hydrocarbon group having from 1 to 8 carbon atoms selected from alkyl, aralkyl and aryl groups, and having from 4 to 50 repeating oxyalkylene units having from 2 to 4 carbon atoms. When component (C) is used, it is sometimes possible to adjust the viscosity of a composition of the present invention without adversely affecting its function as a foam stabilizer or surfactant, and to improve usefulness in applications and handling. Also, component (C) may be added to a polyether-modified silicone composition for the purpose of adjusting the hydroxyl value of a polyurethane foam-forming composition, that is, controlling physical properties such as the crosslinking density and strength of the polyurethane foam.

More specifically, component (C) may be one or more type selected from components (C1) and (C2) based on whether a terminal hydroxyl group has been substituted. A mixture of component (C1) and component (C2) may also be used.

Component (C1) may be a polyalkylene glycol having from 4 to 50 repeating oxyalkylene units having from 2 to 4 carbon atoms (in other words, the degree of polymerization of the polyoxyalkylene moiety) and having hydroxyl groups at both ends of the molecular chain. These compounds are preferably liquid. Typical examples include polypropylene glycols with various degrees of polymerization. The number of repeating oxyalkylene units having from 2 to 4 carbon atoms is preferably from 4 to 35 and more preferably from 6 to 20.

Component (C2) may be a polyalkylene glycol derivative having at least one terminal hydroxyl group substitutable by a hydrocarbon group having from 1 to 8 carbon atoms selected from alkyl, aralkyl and aryl groups, having another unsubstituted hydroxyl group, and having from 4 to 50 repeating oxyalkylene units in the central portion of the molecular chain (provided the oxyalkylene is optionally selected from among those with 2 to 4 carbon atoms). Typical examples include polypropylene glycols monobutyl ethers with various degrees of polymerization. The number of repeating oxyalkylene units having from 2 to 4 carbon atoms is preferably from 4 to 35 and more preferably from 6 to 20.

The amount of component (C) in a composition of the present invention may be in a range from 0 to 300 parts by mass, preferably from 15 to 200 parts by mass, with respect to 100 parts by mass component (A) and component (B). At this time, the viscosity at 25° C. of the entire composition is preferably in a range from 10 to 30,000 mm$^2$/s, and the amounts of component (C) and components (A) and (B) can be adjusted based on the characteristics of the desired polyurethane foam so that the viscosity range is satisfied.

A polyether-modified silicone composition of the present invention may contain water-soluble alcohols other than component (B) and component (C) as long as the technical effects of the present invention are not impaired. Examples of water-soluble alcohols include alcohols and glycols having from 1 to 4 carbon atoms such as ethanol, ethylene glycol, propylene glycol, butylene glycol, dipropylene glycol, tripropylene glycol, diethylene glycol, triethylene glycol, and isopropanol.

Polyether-modified silicone compositions of the present invention are gradually oxidized and denatured by oxygen in air. In order to prevent this, antioxidants such as a phenols, hydroquinones, benzoquinones, aromatic amines, and vitamins are preferably added to increase oxidation stability. Specific examples of antioxidants include BHT (2,6-di-t-butyl-p-cresol), vitamin C, and vitamin E. However, from the standpoint of reducing polyurethane foam emissions, it is important to select vitamin E or some other high molecular weight antioxidant. The amount of antioxidant added is in a range from 10 to 1000 ppm, preferably from 50 to 500 ppm, relative to the polyether-modified silicone in terms of mass.

[Reduction of Low Molecular Weight Siloxane]

In a polyether-modified silicone composition of the present invention, the amount of low molecular weight siloxane having 20 or fewer silicon atoms is preferably 5,000 ppm (by weight) or less, and preferably 2,000 ppm (by weight) or less. When the amount exceeds 5,000 ppm, it may contaminate components where the polyurethane foam is installed and cause contact failure in electrical devices and electronic devices, especially when a polyether-modified silicone composition of the present invention is used as a foam stabilizer for polyurethane foam. The low molecular weight siloxane may be cyclic or linear. Examples include cyclic dimethyl siloxane represented by the formula: $[(CH_3)_2SiO]_n$ (where n is an integer from 3 to 10), a linear dimethylsiloxane oligomer represented by the formula: $CH_3[(CH_3)_2SiO]_mSi(CH_3)_3$ (where m is an integer from 1 to 10), or either one in which some of the methyl groups have been substituted by another organic group. Specific examples of low molecular weight siloxanes include octamethyltetrasiloxane, decamethylpentacyclosiloxane, and dimethyl siloxane oligomers blocked at both ends by a trimethylsiloxy group. The amount of low molecular weight siloxane can be measured using, for example, a gas chromatography analyzer. There are no particular restrictions on the method used to reduce the low molecular weight siloxane. However, in order to do this industrially using a stripping operation, the organic hydrogen polysiloxane used as a raw material in a polyether-modified silicone composition of the present invention is preferably purified beforehand to remove low molecular weight siloxane. Alternatively, low molecular weight siloxane may be removed during or after the hydrosilylation reaction.

[Manufacturing Method]

For a polyether-modified silicone composition of the present invention, the polyether-modified silicone serving as component (A) in the present invention is preferably obtained from a hydrosilylation reaction with an organic hydrogen polysiloxane represented by Formula (1'H) and a polyether compound having an alkenyl group at one end of the molecular chain represented by Formula (2) below:

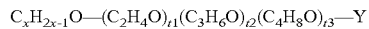

$C_xH_{2x-1}O$—$(C_2H_4O)_{t1}(C_3H_6O)_{t2}(C_4H_8O)_{t3}$—Y

{where x, t1, t2 and t3 are the same numbers as above, Y is defined in the same manner as above, and $C_xH_{2x-1}$ is a linear or branched alkenyl group having a carbon-carbon double bond}. At this time, the step used to initiate or promote the hydrosilylation reaction may be performed without a solvent, in the presence of the monool organic compound serving as component (B), or in the presence of a volatile organic solvent (B') other than component (B). When the step to initiate or promote the hydrosilylation reaction for obtaining component (A) is performed without a solvent or in the presence of a volatile organic solvent (B') other than component (B), a step for adding component (B) is also required.

There are no particular restrictions on the catalyst for the hydrosilylation reaction as long as it can promote the hydrosilylation reaction. Any metal or compound commonly used as a hydrosilylation reaction catalyst can also be used in the present invention. Specific examples of hydrosilylation reaction catalysts include fine particulate platinum adsorbed on a fine silica powder or carbon powder carrier, chloroplatinic acid, alcohol-modified chloroplatinic acid, olefin complexes of chloroplatinic acid, chloroplatinic acid and vinyl siloxane coordination compounds, platinum black, palladium, and rhodium catalysts. These catalysts can be introduced to the reaction system by dissolving or dispersing them in toluene, catalyst ligand compounds, alcohols, other suitable polar solvents, polyether reaction materials, unsaturated compounds and diluents in the usual manner, but are preferably introduced by diluting them in component (B) of the present invention. The catalyst solvent should only be removed if necessary.

There are no particular restrictions on the amount of hydrosilylation reaction catalyst used as long as the amount is an effective amount and promotes the polymerization reaction of the polyether-modified silicone composition of the present invention. Specifically, the metal atoms in the catalyst should be from 0.1 to 300 ppm by mass, preferably platinum metal atoms from 1 to 100 ppm by mass, relative to the total amount of organic hydrogen polysiloxane represented by Formula (1'H) and polyether compound having an alkenyl group on one end of the molecular chain represented by Formula (2) (where the total is 100 mass %). When the amount of hydrosilylation catalyst is below the lower limit of this range, the addition reaction may be insufficient. When the amount is above this range, the additional amount may be uneconomical and may adversely affect transparency or the color of the composition of the present invention obtained in this manner.

As mentioned above, from the standpoint of compatibility with component (B), usefulness as a foam stabilizer, and stability of the polyether-modified silicone composition, component (A) of the present invention preferably has at least one polyoxypropylene unit in the polyether moiety, and the polyether compound represented by Formula (2) preferably has a polyoxypropylene unit. Also, the number of alkenyl groups in the raw material polyether compound is added to the organic hydrogen polysiloxane in an amount equal to or in excess of the number of silicon-bonded hydrogens atom in the organic hydrogen polysiloxane when the hydrosilylation reaction is performed. Specifically, the ratio (molar ratio) of the alkenyl groups ($R^{vi}$) in the polyether compound to silicon-bonded hydrogen atoms (Si—H) in the organic hydrogen polysiloxane is [$R^{vi}$]/[Si—H]=1.0 to 5.00, preferably 1.0 to 2.00, during the reaction. The composition after the reaction may contain unreacted polyether compounds derived from the raw materials.

The conditions in the hydrosilylation reaction depend on the raw materials used and the presence or absence of a solvent, as described below, but a small amount of an antioxidant such as tocopherol (vitamin E) or BHT (butylated hydroxytoluene) may be added, and heating and stirring performed from room temperature to 200° C., preferably from 70 to 150° C., in an inert gas atmosphere such as nitrogen. The antioxidant may be added after completion of the hydrosilylation reaction. The reaction time can be selected based on the reaction scale, the amount of catalyst used, and the reaction temperature, but usually ranges from several minutes to several hours. The reaction may also be performed under reduced pressure to improve quality. For example, the reaction conditions proposed in JP H11-116670 A can be used without any particular restriction.

The end point of the hydrosilylation reaction can be confirmed by the absence of Si—H bond absorption in infrared spectroscopy (IR) or the absence of hydrogen gas generated in the following alkali decomposition gas-generating method. By analyzing the silicone atom-bonded hydrogen atoms (Si—H) in the organic hydrogen polysiloxane reaction raw material using this method, the amount of hydrogen gas generated can be identified.

<Alkali Decomposition Gas Generating Method: A Solution Obtained by Dissolving a Sample in Toluene or IPA is Reacted with a 28.5 Mass % Potassium Hydroxide Ethanol/Water Mixed Solution at Room Temperature, the Generated Hydrogen Gas is Collected in a Collection Tube, and the Volume of the Gas is Measured.>

Also, as long as the technical effects of the polyether-modified silicone composition of the present invention are not impaired, buffers including alkali metal carboxylates such as potassium acetate, potassium propionate, and sodium acetate can be added to suppress side reactions. In order to realize this effect, they can be added as a solid (powder) to the reaction system, dissolved or dispersed in a polar solvent such as methanol or component (B) of the present invention and then added to the reaction system, or dissolved in a polyether compound having an alkenyl group at one end of the molecular chain represented in Formula (2). It is preferably added before initiating the hydrosilylation reaction (main reaction), but may also be added to suppress side reactions that occur after the main reaction, during post-processing, or after manufacturing. The polar solvent used to dissolve, for example, a carboxylic acid alkali metal salt may optionally be removed by stripping before or after the main reaction.

[Optional Purification/Odor Reduction]

Depending on the intended use for the polyether-modified silicone of the present invention, when purification or odor reduction is required for the crude product, any purification method common in the art can be used such as hydrogenation, contact with an acidic substance, or removal of resulting aldehydes. While not limited to these methods, examples include the first and second purification methods proposed in paragraph 0031 of JP 2007-186557A, the odor reduction method proposed in JP 2000-327785 A, and the treatment method using an acid inorganic salt proposed by the present applicant in JP 2011-116902 A. When these purification methods are used, the amount of harmful aldehydes generated by a polyether-modified silicone composition can be minimized beforehand. These purified products are also advantageous from the standpoint of low emissions, and are suitable for use as a foam stabilizer for polyurethane foams used in building materials, in the automotive industry (for example, in automobile interiors), in furniture such as beds and sofas, and in bedding and clothes. These purified products have improved usefulness as cosmetic materials.

[Hydrosilylation Reaction without Solvent—Addition of Component (B)]

A polyether-modified silicone composition of the present invention can be manufactured advantageously using a method comprising at least the steps of initiating a substantially solvent-free hydrosilylation reaction between an organic hydrogen polysiloxane and a polyether compound having an alkenyl group at one end of the molecular chain, and diluting or accelerating the reaction by adding the monool organic compound serving as component (B). The reaction solution can be diluted by adding component (B) after completing the reaction in the absence of a solvent or component (B) can be added during the solvent-free reaction before the reaction is completed. This manufacturing method generally does not require a stripping step. Because a polyether modified silicone of the present invention has excellent performance as a foam stabilizer, foam stabilization is more likely to occur. Therefore, when a reaction is performed in the presence of a solvent, such as toluene, and the solvent is removed under reduced pressure (stripping), the industrial production cycle time may increase over time because the resulting foam does not break up and fills the upper portion of the reaction vessel. Initiating the reaction without a solvent present can eliminate this industrial problem. When a reaction is initiated without a solvent present, and the monool organic compound serving as component (B) is added after the reaction has proceeded to a certain extent, an increase in viscosity due to the addition reaction is suppressed, improving stirring efficiency and reactivity.

[Hydrosilylation Reaction in Presence of Component (B)]

A polyether-modified silicone composition of the present invention can be manufactured advantageously using a method comprising at least the steps of initiating or promoting a hydrosilylation reaction between an organic hydrogen polysiloxane and a polyether compound having an alkenyl group at one end of the molecular chain in the presence of the monool organic compound serving as component (B). In this manufacturing method, a solvent or diluent other than component (B) can be present. If not, a stripping process is not required. When a solvent or diluent other than the component (B) is also present, a stripping step is required only if it has to be removed after the reaction is complete. This method reduces the problem with foaming and the decline in industrial production efficiency mentioned in the previous manufacturing process. When a solvent other than the component (B) is not used, additional steps such as solvent exchange are not required. Because the viscosity of the composition is held down from the start of the reaction, stirring efficiency and reaction efficiency are excellent. This can significantly improve the quality and functionality of the resulting polyether-modified silicone composition when used as a surfactant or foam stabilizer.

[Hydrosilylation Reaction in Presence of a Different Volatile Organic Solvent (B')→Solvent Exchange to Component (B)]

A polyether-modified silicone composition of the present invention can be manufactured advantageously using a method comprising at least the steps of initiating or promoting a hydrosilylation reaction between an organic hydrogen polysiloxane and a polyether compound having an alkenyl group at one end of the molecular chain in the presence of a volatile organic solvent (B') different from component (B), and conducting solvent exchange of the volatile organic solvent (B') with the monool organic compound serving as component (B).

There are no particular restrictions on the volatile organic solvent (B') used in this method as long as it is different from the component (B) and has a boiling point lower than that of the component (B). A boiling point of 60° C. or higher and less than 200° C. can be used. Examples include non-halogenated solvents such as ethanol, i-propyl alcohol, 1-butanol, t-butyl alcohol, cyclohexanol, cyclohexanone, methyl ethyl ketone, methyl isobutyl ketone, isododecane, toluene, xylene, mesitylene, 1,4-dioxane, dibutyl ether, anisole, 4-methylanisole, ethylbenzene, ethoxybenzene, ethylene glycol dimethyl ether, ethylene glycol diethyl ether, 2-methoxyethanol (ethylene glycol monomethyl ether), diethylene glycol dimethyl ether, diethylene glycol monomethyl ether, 1-methoxy-2-propyl acetate, 1-ethoxy-2-propyl acetate, octamethylcyclotetrasiloxane, and hexamethyldisiloxane, as well as halogenated solvents such as trifluoromethyl benzene, 1,2-bis (trifluoromethyl) benzene, 1,3-bis (trifluoromethyl) benzene, 1,4-bis (trifluoromethyl) benzene, trifluoromethyl chlorobenzene, trifluoromethyl fluorobenzene, and hydrofluoroether. These volatile organic solvents can be used alone or in mixtures of two or more.

After the synthesis reaction for a polyether-modified silicone of the present invention has been completed and after the volatile organic solvent (B') has been removed by stripping, solvent exchange can be performed with the monool organic compound serving as component (B). In the hydrosilylation reaction step performed using a volatile organic solvent (B') such as toluene, the foam derived from the polymerized polyether-modified silicone is sometimes stabilized by stirring. In the industrial production process, proper control of the degree of vacuum, the heating temperature, and the stirring speed during stripping is preferred. In order to hold down any increase in production time due to the production of foam during the stripping process, the reaction can be initiated after the pressure has been reduced to a certain degree.

There are no particular restrictions on the solvent exchange method. For example, in a hydrosilylation reaction step using a volatile organic solvent (B') such as toluene, solvent exchange may be performed with the monool organic compound serving as component (B) after the organic solvent has been removed using a rotary evaporator as described in JP H08-156143 A.

As mentioned above, the liquid polyether-modified silicone in the present invention can be produced using many different methods. However, from the standpoint of making the production process more efficient by avoiding the foaming problem, a process that does not include the stripping process is preferred. A process in which the hydrosilylation reaction is initiated in the presence of component (B) is especially preferred.

In particular, the synthesis reaction for a liquid polyether-modified silicone of the present invention can be performed using a continuous hydrosilylation process using component (B) of the present invention and optionally component (C). A continuous hydrosilylation process performed in the presence of component (B) can be applied to the synthesis of polyether-modified silicone compositions that are based on organic hydrogen polysiloxane, which has a relatively high degree of polysiloxane polymerization and a relatively high viscosity. As in the case of the batch process, a polyether-modified silicone composition with excellent quality and emulsification/foam control performance can be produced continuously in large quantities at low cost.

[Uses for Compounds of the Present Invention: Surfactants, Etc.]

Because a polyether-modified silicone composition of the present invention has a silicone moiety and polyether moiety that have different hydrophilic properties from each other in the molecule, they can be used without restriction in any application using a conventional polyether-modified silicone. In other words, it can be used without restriction in a surfactant, foam stabilizer, fiber lubricity agent, or reactive raw material with other polymeric materials. Also, because a polyether-modified silicone of the present invention has excellent compatibility with the specific monool organic compound serving as the component (B) dispersion medium and because the composition as a whole is excellent in terms of industrial productivity, usefulness, compounding stability, handling and workability, and storage stability, it can be readily used in large quantities even in fields that have not yet experienced improvements in terms of cost, handling, and workability. In particular, a polyether-modified silicone composition of the present invention is useful as a surfactant for industrial or cosmetic use, and can be used in paints, coatings, building materials, cosmetics, hydrophilicity imparting agents, surface treatment agents, and foamable resin compositions. There are no particular restrictions. Moreover, deriving from its function as a surfactant, a composition of the present invention can be used as an additive for paints, an emulsifier, a solubilizer, a foam stabilizer for polyurethane foam, or a cosmetic raw material.

[Uses for Compounds of the Present Invention: Foam Stabilizers]

A polyether-modified silicone composition of the present invention can be used advantageously as a surfactant for foam control and stabilization, that is, as a foam stabilizer, in the production of a foamable resin, especially a polyurethane foam. In particular, a composition of the present invention can be used to control the open cell rate (control of air permeability of the foam), not just as a simple cell stabilizer. The homogeneity and stability of the premix solution are excellent, and compatibility with the components in an emulsion composition used to form a foam is also excellent. Furthermore, when this is used with an (AB)n-type polyether-polysiloxane block copolymer composition described in JP H08-156143 A, cell retention and microcellification, that is, cell retention and low-density foam, can both be achieved in microcellular applications and slow recovery foam applications. In a flexible foam application, the desired air permeability can be achieved by adjusting the blending ratio of component (A) and component (B) in the present invention. In rigid foam applications, the closed cell rate and cell size can be controlled by adjusting the mixing ratio of component (A) and component (B) in the present invention.

In a polyether-modified silicone composition of the present invention, the component (B) dispersion medium can be selected based on the degree of siloxane polymerization of the organic hydrogen polysiloxane raw material used in the synthesis reaction. The overall molecular weight of the polyether-modified silicone and the number of polyether-modified groups that are introduced can be easily designed and adjusted. In addition, the surface activity and affinity to a urethane foam system can be controlled by adjusting the EO/PO % and size of the polyether portion and introducing a hydroxyl group or hydrophobic group to the polyether-modified end group portion. In particular, a polyether-modified silicone composition of the present invention obtained from a hydrosilylation reaction performed in the presence of component (B) generally has fast reaction rate and does not require a high-temperature stripping step. As a result, the progress of side reactions that have an adverse effect on performance can be minimized. As a result, the modified silicone exhibits excellent effects as a surfactant for cell control or cell stabilization that are stable and reproducible in all polyurethane foam formulations requiring a design in which the molecular weight of the foam stabilizer is very low. Examples of these formulations include high resilience foams and rigid foams requiring intermediate molecular weight foam stabilizers, flexible foams requiring high molecular weight (highly viscous liquid) foam stabilizers that are difficult to use in stable production, and microcellular foam.

A polyether-modified silicone composition of the present invention can use a wide selection of production steps, and foam control problems either do not occur or are easily eliminated during the production process when the desired polyether-modified silicone has been designed. Productivity is excellent, manufacturing and application issues linked to industrial production costs have been comprehensively solved, foam stabilizers containing a novel polyether-modified silicone composition can be fully introduced on the market, and high-performance raw materials can be used.

[Polyurethane Foam-Forming Composition]

These foam stabilizers are used in the manufacture of polyurethane foam. Therefore, a polyurethane foam-forming composition of the present invention is not limited with respect to type, characteristics, and applied formulation as long as it contains a polyether-modified silicone composition of the present invention as a foam stabilizer.

[Types of Foam]

Polyurethane foams are generally classified as rigid or flexible. More specifically, they are roughly classified as soft urethane foams, high resilience urethane foams, rigid urethane foams, and special-purpose foams. Because polyurethane foam-forming compositions of the present invention are excellent in terms of molecular weight design and handling, they have excellent effects as a foam stabilizer in all polyurethane foam formulations.

Flexible urethane foams are widely used as cushioning materials in sofas and beds, and in sheets for use in automobiles. Because the raw material viscosity in flexible slab foam is relatively low and the expansion ratio is high, the stabilization of cell membranes during cell growth is key. Relatively high molecular weight foam stabilizers (polyether-modified silicones) are well suited to these systems. In order to ensure compatibility with No. 3000 polyol, graft-modified polyethers having a relatively high propylene/oxide ratio are widely used. Because the type whose modified-polyether end is uncapped (hydroxyl group) has a closed cell-strengthening effect, the type whose polyether end is capped (usually methoxy-capped) is widely used to help facilitate cell membrane communication. A polyether-modified silicone composition of the present invention is a surfactant with a relatively high molecular weight and a low-emission (or low-fogging) foam stabilizer containing one of the aforementioned monool organic compounds, and can be used advantageously in this system. A flexible hot mold formulation consists of a urethane stock solution system similar to a soft slab formulation and has high reactivity. It is important to ensure high air permeability because it is packed in a mold. A polyether-modified silicone composition of the present invention can be used to realize high air permeability and can be used in such a formulation.

Flame retardant foam-compatible foam stabilizers are defined as those that reduce the amount of flame retardant added during formulation and those that reduce the adverse effects of adding a flame retardant on foam properties. However, silicone foam stabilizers are generally positioned as a flame retardant. This is because a silicone foam stabilizer collects on the liquid surface of a heat-melted foam due to the surface active effect and prevents carbonization. Therefore, a foam control agent having a relatively low silicone content and lower foam control activity is suitable for use in a flame retardant foam. A polyether-modified silicone composition of the present invention may be used as a flame retardant foam-compatible foam stabilizer.

Because high resilience (HR) foam is primarily used as molded foam for automobile seats, there is demand for improved moldability and air permeability. Cell membrane stabilization is relatively easy in HR foam because the system viscosity and reactivity are high. Because communication does not occur, problems such as cracking due to accumulated gas inside the foam and shrinkage after release from the mold have to be prevented. For this reason, foam control agents with very weak foam control and good cell opening properties are widely used. This type of foam stabilizer is designed to have a very low molecular weight and is characterized by early component emulsification and very weak cell membrane retention.

In this system, a relatively low molecular weight dimethylpolysiloxane with unmodified polyether is also used. When combined with a polyether-modified silicone, these can function as a foam control agent that imparts stable foam control activity (moldability), and can adjust the cell openness and foam control strength by optimizing the molecular weight distribution.

TDI-based formulations that require high activity include those that impart strong foam control and fine cell ability, and MDI-based formulations that require relatively strong closed cell activity include those that impart weak cell control, good crushing properties, and high air permeability. When strong and weak foam control are combined, cell size and air permeability are adjusted. This system-specific technique is widely used in production.

However, very low molecular weight polyether-modified silicones and low molecular weight dimethylpolysiloxanes, which are widely used in high resilience foam applications, have a narrow processing range (the degree of freedom and tolerances in foam formulation are narrow). A suitable amount of a polyether-modified silicone composition can be included to solve this problem.

Rigid urethane foams are widely used as heat insulating materials in construction and refrigerators because they are light-weight, have excellent thermal insulation properties, and have high productivity. In order to improve the thermal insulation properties of rigid urethane foams, the cell size has to be as small as possible. The number of cells in the final foam and the number of entrained gas bubbles dispersed during initial stirring of the urethane foaming liquid are almost identical. Therefore, a foam control agent that enhances emulsification during the initial stirring is ideal. However, the foam is more likely to shrink when the cells are finer. Here, shrinkage is prevented by using a relatively low foaming activity formulation and by increasing cell size. Also, polyisocyanurate foams with excellent flame retardance are classified as a type of rigid urethane foam.

HCFC 141b, which was used as a blowing agent in rigid polyurethane foams in the past, is now regulated to protect the environment, and the HFC compounds that have been used as a substitute will probably be regulated in the near future. The effect of blowing agents on urethane foam formulation is significant, and the most suitable foam stabilizer has to be selected based on the type of foam.

In HFC formulations using a large amount of water, the initial emulsifying power is lower than that of HCFC-141b formulations which are more compatible with the urethane stock solution systems. Therefore, good cells can be obtained by formulating a foam control agent with high foam control activity. In cyclopentane formulations, there are cases in which premix compatibility is required from the standpoint of storage stability. In this case, compatibility with the base polyol is important, and those with a high EO (ethylene oxide) ratio with the modified polyether and a terminal hydroxyl group (—OH) exhibit relatively good compatibility. Because composition of the present invention has excellent compatibility with polyurethane foam-forming compositions using HFC and cyclopentanes, blowing agents that function as effective foam stabilizers can be formulated for rigid polyurethane foam formulations or premixes. Also, because compositions of the present invention are low emission (or low VOC) foam stabilizers, they are expected to have an effect that reduces or alleviates the problem of sick building syndrome.

A polyether-modified silicone composition of the present invention is preferably a foam stabilizer comprising a medium to relatively high molecular weight surfactant and a specific monool organic compound. If desired, the emulsifiability, molecular weight, and terminal functional groups can be adjusted. As a result, it can be used without restriction even in water-foamed rigid urethane foams.

Special-purpose foams include semi-rigid foams which are intermediate materials between flexible foams and rigid foams, low-resilience foam which are derived from flexible foams but have unique applications and status due to their unique visco-elastic behavior, high density foams known as integral skin which are used in the soles of shoes, and microcellular foams produced using a mechanical foaming (mechanical froth) method.

In addition, foams produced using polyester-type polyols rather than the polyether-type polyols commonly used as raw material polyols in urethane foams, are known as ester foams, these are classified according to the foam characteristics as described above.

Because rigid foams emphasize thermal insulation in most applications, closed cell foams with a high closed cell rate are usually required. However, in some applications, emphasis is placed on dimensional stability, and surfactants and foam composition formulations are selected to produce a partial open-cell foam. In all-purpose flexible foams, a polyurethane structure is formed by reacting a polyol and an isocyanate, and foaming is due to reaction heat and a blowing agent. These are designed so that all cell (air pocket) membranes in the structure rupture (open) and communicate (continuous ventilation) at the moment when the structure stops increasing in strength due to crosslinking.

Although the formulation of low resilience foams is similar to that of all-purpose flexible foams, structural elements with viscoelasticity are incorporated into the raw material polyol. For this reason, it is difficult to get cells to communicate and the importance of surfactants with a high cell opening effect is increasing. In the field of high-density microcellular foams obtained by HR and mechanical foaming methods, various applications have been created by controlling the open cell rate.

A polyether-modified silicone composition of the present invention is a foam control agent that can be used to control the open cell rate, and can be used not only as a foam stabilizer but also to control the open cell rate even in high density microcellular foams obtained by mechanical foaming and in other rigid foams and flexible foams.

Preferably a polyurethane foam-forming composition of the present invention comprises:
(a) a polyol;
(b) a polyisocyanate;
(c) a catalyst;
(d) a foam stabilizer containing a polyether-modified silicone composition according to any one of claims 1 to 7; and
(e) optionally at least one additional component selected from a group consisting of a foam stabilizer other than component (d), a blowing agent, a diluent, a chain extender, a crosslinker, water, a non-aqueous blowing agent, a filler, a strengthening agent, a pigment, a dye, a colorant, a flame retardant, an antioxidant, an anti-ozone agent, an ultraviolet light stabilizer, an antistatic agent, a fungicide, and an antimicrobial agent. The following is a description of each component.

[(A) Polyol]

Examples of polyols include polyether polyols and polyester polyols. Examples of polyether polyols include those obtained by adding an alkylene oxide to a polyhydric alcohol, saccharide, phenol, phenol derivative, or aromatic amine. Specific examples include those obtained by adding an alkylene oxide to one or two types among glycerin, propylene glycol, dipropylene glycol, ethylene glycol, diethylene glycol, trimethylol propane, pentaerythritols, sucrose, sorbitol, novolacs, nonylphenol, bisphenol A, bisphenol F, tolylene diamine, and diphenylmethanediamine. Examples of polyester polyols include polyols with a terminal hydroxyl group produced by condensation polymerization of a polyfunctional carboxylic acid such as adipic acid, phthalic acid or succinic acid, and a multifunctional hydroxyl compound such as glycerin, propylene glycol, dipropylene glycol, ethylene glycol, diethylene glycol, trimethylol propane, or pentaerythritol. The polyols may be used alone or in combinations of two or more. From the standpoint of imparting low emission properties to a polyurethane foam, it is important to select high molecular weight non-volatile additives (such as antioxidants and stabilizers) to be included in the polyol.

Preferred polyols for preparing polyurethane foams of the present invention have from 2 to 8 hydroxy group per molecule and have a number average molecular weight from 200 to 10,000, preferably from 500 to 7,500. Examples of useful polyether polyols include Voranol 220-028, Voranol 220-094, Voranol 225, Voranol 270, Voranol 490, and Voranol 800 (Dow Chemical Company) as well as Arcol 11-34 (Bayer Material Science).

Polyols such as polyether polyols and polyester polyols usually have a hydroxyl number (hydroxyl value) in a range from about 15 to about 700. The hydroxyl number is preferably about 20 to 60 for flexible foam, about 100 to 300 for semi-flexible (or semi-rigid) foam, and about 250 to 700 for rigid foam. In flexible foams, the preferred functional value, that is, the average number of hydroxyl groups per polyol molecule in the polyol, is from about 2 to about 4, and more preferably from about 2.3 to about 3.5. In rigid foams, the preferred functional value is from about 2 to about 8, and more preferably from about 3 to about 5.

A foam stabilizer of the present invention can be used as a foam stabilizer in most polyurethane foams. The amount used is from 0.3 to 8.0 parts by mass polyether-modified silicone (A) in the polyether-modified silicone composition per 100 parts by mass polyol, preferably from 0.5 to 4.0 parts by mass, and more preferably from 1.0 to 2.0 parts by mass.

[(b) Polyisocyanate]

Any organic polyisocyanate common in the art can be used as the polyisocyanate. The most common examples are tolylene diisocyanate ("TDI" below) and diphenylmethane diisocyanate ("MDI" below). TDI is a mixture of isomers, that is, 100% 2,4-isomer, 2,4-isomer/2,6-isomer=80/20, 65/35 (mass ratio of each). Crude TDI containing multifunctional tar can also be used. The MDI can be a pure product composed primarily of 4,4'-diphenylmethane diisocyanate, or polymeric MDI containing a trinuclear polynuclear substance or higher.

Among these isocyanate compounds, MDI is often used to produce rigid polyurethane foams and TDI is often used to produce flexible polyurethane foams.

MDI isocyanate prepolymers are obtained by reacting MDI with a polyol, modified using, for example, uretone imine modification, and combined with the MDI derivatives described above in any proportion. Toluene diisocyanate (TDI) can also be used. This includes isocyanate prepolymers of TDI obtained by reaction 2,4- and 2,6-isomers and TDI with polyols, and modified versions such as polyisocyanates and prepolymers thereof modified using other aromatic or aliphatic polyisocyanates or uretone imine. Mixtures of polyisocyanates are also within the scope of the present invention.

The amount of polyisocyanate added to a formulation relative to the amounts of other materials is represented by the "isocyanate index." The "isocyanate index" is the actual amount of the polyisocyanate used divided by the stoichiometric amount of polyisocyanate required for a reaction with all of the active hydrogen in the reaction mixture multiplied by 100. The isocyanate index for a polyurethane foam-forming composition used in a method of the present invention is generally from 60 to 140. Typically, the isocyanate index is from 85 to 120 for flexible TDI foams, from 90 to 105 for molded TDI foam or high resilience (HR) foams, from 70 to 90 for molded MDI foams, and from 90 to 130 for rigid MDI foams. Some polyisocyanurate rigid foams are manufactured with a high index from 250 to 400.

[(c) Catalyst]

Examples include nickel acetoacetonate, iron acetoacetonate, tin-based catalysts, bismuth-based catalysts, zinc-based catalysts, titanium-based catalysts, aluminum complexes, zirconium complexes, potassium octylate, potassium acetate, sodium acetate, sodium octylate, metal oxide particles with solid acid sites on the surface, triethylenediamine, tertiary amine urethane catalysts such as bis (dimethylaminoethyl) ether, imidazole derivatives, carboxylic acid quaternary ammonium salts, slow-acting tertiary amine catalysts, general tertiary amine catalysts, low-emission tertiary amine catalysts, non-emission tertiary amine catalysts, and DABCO (registered trademark) catalysts from Air Products.

Among these catalysts, amine-based catalysts are preferred in the production of rigid polyurethane foams and combinations of amine-based catalysts and tin-based catalysts are preferred in the production of flexible polyurethane foams.

[(d) Foam Stabilizer Containing a Polyether-Modified Silicone Composition of the Present Invention]

In polyether-modified silicone compositions of the present invention described above, there is usually a correlation or compatibility between the type of silicone used in the polyether portion of a foam stabilizer and the type of foam resin. The following is the order from foams in which low molecular weight foam stabilizers are suitable to foams in which high molecular weight foams are suitable: high resilience foams<rigid foams<flexible foams<microcellular foams.

Because the structure of the polyether moiety in a foam stabilizer molecule has a significant effect on foam size, the following techniques can be applied to a polyether-modified silicone composition of the present invention, namely, selecting a polyether structure with high EO content to reduce cell size and air permeability, selecting a polyether with a high molecular weight to stabilize and retain air bubbles, expanding the processing range, and expanding the molecular weight distribution of the polyether moiety such as using polyethers with different molecular weights and structures in the raw material in order to expand compatibility within a wider range of applications and prescriptions. It is often desirable to include a polyol with a PPG structure among the primary polyurethane raw materials, and include a PO (propyleneoxy) chain in the polyether moiety of the polyether-modified silicone in a foam formulation from the standpoint of compatibility.

These requirements depend on the type of polyurethane foam in which a polyether-modified silicone composition of the present invention is used. However, surface activity and affinity to urethane foam systems can be controlled by adjusting the type of organic hydrogen polysiloxane represented by Formula (2) and the type of polyether with terminal alkenyl groups represented by Formula (3), by adjusting the reaction ratio, by adjusting the EO/PO % and size of polyether moiety, and by introducing a hydroxyl group or a hydrophobic group to the end of the copolymer. This allows a foam stabilizer to be designed with a greater degree of freedom.

[(e) Optional Components]

Water and a non-aqueous blowing agent are of particular importance among the optional components (e) in a polyurethane foam-forming composition. Water acts as a chemical blowing agent by reacting with the polyisocyanate to form carbon dioxide gas. One or more non-aqueous physical or chemical blowing agents can also be included in the reaction mixture. There are some formulations in which water is not used. Examples of these blowing agents include hydrofluorocarbons such as HFC-245fa and HFC-134a, hydrofluoroolefins such as HFO and HCFO, low boiling point hydrocarbons such as iso-, cyclo- and n-pentane, supercritical carbon dioxide, and formic acid.

Water is frequently used as a reactive blowing agent in both flexible and rigid foams. In the production of flexible slab foams, water can be used at a concentration from 2 to 6.5 parts, typically from 3.5 to 5.5 parts, per 100 parts polyol. The amount of water in a TDI molded foam or high resilience (HR) foam is typically from 3 to 4.5 parts. The amount of water in an MDI molded foam is typically from 2.5 to 5 parts. The amount of water in a rigid foam can be from 0.5 to 5 parts, typically from 0.5 to 1 part. Physical blowing agents, such as blowing agents based on volatile hydrocarbons, halogenated hydrocarbons or other non-reactive gases, can also be used to produce a polyurethane foam of the present invention. The rigid insulating foams are foamed using a substantial amount of volatile hydrocarbons or halogenated hydrocarbons. Preferred blowing agents include hydrochlorofluorocarbons (HCFCs) and volatile hydrocarbons such as pentane and cyclopentane. Hydrofluoroolefins (HFO, HCFO) can also be used. In the production of flexible slab foam, water is the primary blowing agent, but other blowing agents can be used as auxiliary blowing agents. For flexible slab foams, preferred auxiliary blowing agents include carbon dioxide and dichloromethane. High resilience (HR) foams either do not use inert auxiliary blowing agents or use less auxiliary blowing agent than slab foams. However, in some molding techniques, the use of carbon dioxide is critical. The amount of blowing agent used varies depending on the desired foam density and foam hardness. The amount of hydrocarbon blowing agent used can range, for example, from a trace amount to 50 parts per 100 parts polyol, and $CO_2$ is, for example, from about 1 to about 10%.

However, in microcellular applications especially, polyurethane foams in which chemical foaming is performed using water, pyrofluorocarbons, and low boiling point hydrocarbons as foaming agents, the hardness can be too low, the dimensional accuracy required for the final product can be difficult to obtain, and the mechanical strength such as tensile strength and abrasion resistance can be insufficient. Therefore, high-density foams are usually produced using mechanical foaming. Here, air or nitrogen gas introduced by mechanical stirring forms the nuclei of air bubbles.

The polyol a), polyisocyanate b), catalyst c), polyether-modified silicone composition of the present invention d), and optional components e) such as water and non-aqueous blowing agents used to obtain a polyurethane foam-forming composition can be altered within the wide ranges indicated below. The reason for these wide ranges is to allow for formulation of a polyurethane foam-forming composition to be adjusted based on the properties of the foam, the intended application, the type of foam, and the equipment used.

An example of composition ranges for a polyurethane foam-forming composition is the following: 6 to 85 parts by mass of polyol a), 10 to 80 parts by mass of polyisocyanate b), 0.01 to 5.0 parts by mass of catalyst c), 0.1 to 20 parts by mass of polyether-modified silicone composition of the present invention d), and optionally 0 to 9 parts by mass of water and 0 to 45 parts by mass non-aqueous blowing agent.

The mass amount of water that can be contained in the polyurethane foam-forming composition is preferably in a mass equivalent range from 0 to 10% relative to the polyol.

Other optional components e) include any additives common in the art. Examples include other polymers and/or copolymers, diluents, chain extenders, crosslinking agents, fillers, reinforcing agents, pigments, dyes, colorants, flame retardants, antioxidants, anti-ozone agents, UV light stabilizers, antistatic agents, fungicides, and antimicrobial agents. These can be included within the usual ranges. From the standpoint of imparting low emission characteristics, optional components must be composed only of materials that do not migrate or volatilize from foam. It is important to the design of a polyurethane foam-forming composition to have such materials compounded in the foam formulation.

These optional components e) include polyhydroxyl-terminated compounds with from 2 to 8 hydroxyl groups per molecule and a molecular weight from 62 to 500 serving as crosslinking agents or chain extenders. Crosslinking agent having from 3 to 8 hydroxyl groups per molecule include glycerin, trimethylolpropane, pentaerythritol, mannitol, and sorbitol. Examples of useful chain extenders having two hydroxyl groups include dipropylene glycol, tripropylene glycol, propylene glycol, diethylene glycol, triethylene glycol, 1,4-butanediol, ethylene glycol, 2,3-butanediol, 2-methyl-1,3-propanediol, 1,2-propanediol, 1,3-propanediol, and neopentyl glycol. Diethanolamine and monoethanolamine can also be used.

These optional components e) also include fillers, such as, mineral fillers and combinations of fillers. Fillers are used to improve density, physical performance such as mechanical performance and sound absorption, flame retardancy, and cost performance such as calcium carbonate. Others include fillers that reduce the cost of foam production aluminum hydroxide and other flame retardant fillers, barium sulfate and other high density fillers used for sound absorption, and glass and polymer microspheres to further reduce foam density. High aspect ratio fillers and reinforcing agents used to improve mechanical performance such as the rigidity and flexibility of foam include artificial fibers such as crushed glass fibers and graphite fibers, natural mineral fibers such as wollastonite, animal fibers such as wool, plant fibers such as cotton, artificial plate-like fibers such as crushed glass, and natural mineral plate-like fillers such as mica. Pigments, dyes, and colorants may also be added. In the present invention, when organic flame retardants, antiozonants, antioxidants, heat and heat-oxygen decomposition inhibitors, UV stabilizers, and UV absorbers are to be added to a foam-forming composition, any additive that prevents or inhibits heat, light and/or chemical degradation of the resulting foam can be considered. Any antistatics, bactericides, antimicrobials and gas fading inhibitors common in the art can also be included.

The polyurethane foams obtained from a polyurethane foam-forming composition of the present invention are preferably rigid foams, semi-rigid foams, high resilience (HR) foams, flexible foams, and microcellular foams.

Existing production methods can be used in the process of producing polyurethane foams from polyurethane foam-forming compositions of the present invention. For example, in the case of flexible foams, polyurethane foams can be produced using the one-shot foaming method, the quasi-prepolymer method, or the prepolymer method. Flexible foams are usually produced industrially as slab foams. Some slab foams are produced by injecting the reactant mixture into a large box (a discontinuous method known as box foaming), but conventional slab stock foams are manufactured continuously by discharging the reaction mixture onto a paper-lined conveyor. Foaming and hardening occurs as the conveyor advances, and the foam is cut into large blocks while exiting from the foamer.

In the case of rigid foam, the manufacturing method depends on the intended purpose and application. For example, "spray foaming" is a system in which a polyurethane foam-forming composition is sprayed, foamed, and solidified on site. "Laminated boards" are used primarily as a thermal insulation material in prefabricated buildings. These are also known as "insulating boards" and "continuous lamination board stock." In the production of a laminated board, a foamed foam-forming composition is continuously supplied via rollers between vertical surface materials facing each other, and is cured while flowing to obtain a final board having a thickness of about 10 cm. "Appliance foam" is a foam used exclusively to insulate refrigerators, and is produced by a fully automated injection molding process in a plant. In this case, the foam-forming composition is injected into a mold where it foams and is cured. The foam is not removed from the mold until the process is completed. A feature of refrigerator foam is that water is not used as a foaming agent in order to improve heat insulating properties (because carbon dioxide readily transmits heat). "On-site injection" is a system in which a foam-forming composition is injected into a mold on site where it foams and is cured. This refers to applications other than refrigerators.

A "microcellular foam" is a special-purpose homogeneous, fine, high-density foam produced using a mechanical foaming system known as a mechanical froth system. Here, blowing agents are not used. Instead, air or nitrogen gas is introduced by mechanical stirring to form the nuclei of the air bubbles.

The low resilience foam is a type of special-purpose foam or flexible foam and is manufactured in slab or mold form like other flexible foams and HR foams. In a slab product, the stock mixture is poured onto a continuous conveyor. Usually, a slab with a cross-sectional width from 1 to 2 m and height from 0.2 to 0.6 m is continuously foamed in a square or round shape, and then cut to a predetermined length (usually 1 to 2 m) in the shape of a bread pan. These slabs are usually shipped to a processing site in this form, where products of various shapes are cut out and processed from slabs. Molded products are prepared by pouring a stock solution into a plastic or metal mold for foaming, and then removed from the mold. Products with complex shapes can be molded in large quantities with high dimensional accuracy.

While the appropriate polyurethane foam manufacturing method can be selected, a polyether-modified silicone composition of the present invention can replace a silicone-based foam stabilizer, silicone-based surfactant, or silicone-based copolymer surfactant in any polyurethane foam production method described in the specification of any of the following patent publications, especially in the examples. Note that the manufacturing devices are disclosed in the specifications and examples of these patent documents.

Some of the components can be replaced and some of the manufacturing conditions changed by those skilled in the art to change, for example, the viscosity.

The production method for polyurethane foam described in JP 2005-534770 A, JP 2005-534770 A, and JP 2010-535931 A The production process for open cell polyurethane described in JP 2010-539280 A The sealing material containing urethane foam described in JP 2012-246397 A and JP 2009-265425 A The production process for urethane foam described in JP 2012-082273 A, JP 2010-247532 A, JP 2010-195870 A, and JP 2002-137234 A Polyurethane foams obtained by applying a polyether-modified silicone composition of the present invention to the production methods in these patent publications are included within the scope of the present invention. Needless to say, the scope of the present invention for polyurethane foams using polyether-modified silicone compositions of the present invention is not limited to these examples.

[Cosmetic Raw Materials and Cosmetics]

A polyether-modified silicone composition of the present invention is useful as a cosmetic raw material and, as described above, it can be produced at relatively low cost in an industrial production process, and can be supplied at high added value and at a low price.

The present invention also relates to a cosmetic containing such a polyether-modified silicone composition. These cosmetics include cosmetic compositions containing polyether-modified silicones, glycerin-modified silicones or polyether-modified silicones common in the art, cosmetic raw material components for these cosmetics, combinations of these components, and uses for these components.

Specific examples include skin cosmetics and hair cosmetics containing a polyether-modified silicone composition of the present invention.

There are no particular restrictions on the form of a skin cosmetic of the present invention as long as it contains a polyether-modified silicone composition of the present invention. It can assume the form of a solution, cream, solid, semi-solid, gel, or water-in-oil emulsion composition, or oil-in-water emulsion composition. More specifically, a skin cosmetic of the present invention can be a basic cosmetic such as a lotion, emulsion, cream, sunscreen emulsion, sunscreen, hand cream, cleanser, massage liquid, cleaning agent, antiperspirant, or deodorant. It can also be a makeup cosmetic such as a foundation, makeup base, blush, lipstick, eye shadow, eyeliner, mascara, or nail enamel.

Similarly, a hair cosmetic composition of the present invention can assume various forms as long as it contains a polyether-modified silicone composition of the present invention. For example, it may be dissolved or dispersed in an alcohol, hydrocarbon or volatile cyclic silicone, or may be dispersed in water using an emulsifying agent and used in the form of an emulsion. It can also be combined with a propellant such as propane, butane, trichloromonofluoromethane, dichlorodifluoromethane, dichlorotetrafluoroethane, carbon dioxide gas or nitrogen gas and used as a spray. Other forms include shampoos, rinses, set lotions, hair sprays, permanent wave agents, mousses, and hair dyes.

A cosmetic of the present invention can include any additive commonly used in cosmetics. Examples include water, powders and colorants, alcohols, water-soluble polymers, film-forming agents, oils, oil-soluble gelling agents, organically modified clay minerals, surfactants, resins, UV absorbers, moisturizers, preservatives, antibacterial agents, perfumes, salts, antioxidants, pH adjusters, chelating agents, refreshing agents, anti-inflammatory agents, skin care ingredients (whitening agents, cell activators, rough skin improvers, blood circulation promoters, skin astringents, anti-seborrheic agents, etc.), vitamins, amino acids, nucleic acids, hormones, clathrate compounds, physiologically active substances, and fragrances. A polyether-modified silicone composition of the present invention can be used as a substitute in cosmetic formulations containing conventional polyether-modified silicones, glycerin-modified silicones, sugar-modified silicones, and polyether-modified silicones. There are no particular restrictions. Various components that can be added to a cosmetic of the present invention and formulations thereof are found in the specification of Patent Document 11 (WO 2011/049248 A1).

[Formulations Already Disclosed in Prior Application]

A polyether-modified silicone composition of the present invention can be used in various external preparations and cosmetics. In a specific example of a formulation, a polyether-modified silicone composition of the present invention can replace the appropriate component in the silicone-based surfactants used in the formulated examples of cosmetics and external preparations disclosed by the present applicant in the examples described in Patent Document 11 (WO 2011/049248 A1). The formulated examples of cosmetics and external preparations in this patent document are included in the scope of the present invention. Needless to say, the present invention is not limited to these formulated examples of cosmetics and external preparations. A polyether-modified silicone composition of the present invention can replace any silicone-based surfactant for a cosmetic containing conventional silicone-based surfactants (polyether-modified silicones, glycerin-modified silicone, and polyether-polysiloxane block copolymers), and these formulated examples of cosmetics and external preparations are included in the scope of the present invention.

EXAMPLES

The following is a more detailed description of the present invention with reference to examples and comparative examples. Note that the present invention is not limited to these examples. In the compositional formulas, Me is a methyl group, M is a $Me_3SiO$ group (or $Me_3Si$ group), D is a $Me_2SiO$ group, $M^H$ is a $Me_2HSiO$ group, and $D^H$ is a MeHSiO group. Units in which the methyl group in M or D has been modified by a substituent are denoted by M* or D*. Also, IPA is isopropyl alcohol.

<Example 1-1> Surfactant Usable in Both Rigid and Flexible Foams

A 500-mL reaction vessel was charged with 43.78 g of a SiH group-containing organopolysiloxane represented by an average composition formula of $MD_{43.3}D^H{}_{6.7}M$, 184.22 g of a one-ended allyl polyether represented by an average composition formula of $CH_2=CH-CH_2-O(C_2H_4O)_{24}(C_3H_6O)_6-CH_3$, and 10 g of dipropylene glycol monobutyl ether (BuDPG), and the temperature was raised to 93 to 98°

C. while stirring the contents under a nitrogen flow. The allyl/SiH mass ratio in the hydrosilylation reaction was 1.567. Once 2.0 g of a BuDPG solution of platinum-2,4,6,8-tetramethyl-2,4,6,8-tetravinyl tetrasiloxane complex (Pt concentration: 0.01 wt %) had been added, the reaction solution was clear within 35 minutes. The reaction was conducted for a total of 2.5 hours. Next, 1 g of reaction solution was collected and completion of the reaction was verified using the alkali decomposition gas generation method.

In this way, a polyether-modified silicone composition was obtained in the form of a clear, homogeneous liquid in which the ratio of polyether-modified silicone represented by an average composition formula $MD_{43.3}D^*_{6.7}M$ {where, $*=-C_3H_6O(C_2H_4O)_{24}(C_3H_6O)_6-CH_3$} to unreacted polyether to BuDPG was 67.2:27.8:5. Here, the polyether moiety was a random adduct of ethylene oxide and propylene oxide. (Yield: 235 g)

<Example 1-2> Surfactant Usable in Both Rigid and Flexible Foams

A 500-mL reaction vessel was charged with 40.8 g of a SiH group-containing organopolysiloxane represented by an average composition formula of $MD_{43.3}D^H_{6.7}M$, 171.7 g of a one-ended allyl polyether represented by an average composition formula of $CH_2=CH-CH_2-O(C_2H_4O)_{24}(C_3H_6O)_6-CH_3$, and 35 g of dipropylene glycol monobutyl ether (BuDPG), and the temperature was raised to 92° C. while stirring the contents under a nitrogen flow. The allyl/SiH mass ratio in the hydrosilylation reaction was 1.567. Once 2.5 g of a BuDPG solution of platinum-2,4,6,8-tetramethyl-2,4,6,8-tetravinyl tetrasiloxane complex (Pt concentration: 0.02 wt %) had been added, the reaction solution was clear within 30 minutes. The reaction was conducted for a total of 2.5 hours. Next, 1 g of reaction solution was collected and completion of the reaction was verified using the alkali decomposition gas generation method.

In this way, a polyether-modified silicone composition was obtained in the form of a clear, homogeneous liquid in which the ratio of polyether-modified silicone represented by an average composition formula $MD_{43.3}D^*_{6.7}M$ {where, $*=-C_3H_6O(C_2H_4O)_{24}(C_3H_6O)_6-CH_3$} to unreacted polyether to BuDPG was 60:25:15. Here, the polyether moiety was a random adduct of ethylene oxide and propylene oxide. (Yield: 242 g)

<Example 1-3> Surfactant Usable in Both Rigid and Flexible Foams

A polyether-modified silicone composition was obtained in the form of a clear, homogeneous liquid in which the ratio of polyether-modified silicone represented by an average composition formula $MD_{43.3}D^*_{6.7}M$ {where, $*=-C_3H_6O(C_2H_4O)_{24}(C_3H_6O)_6-CH_3$} to unreacted polyether to BuDPG was 53:22:25 by weighing out 25.0 g of the polyether-modified silicone composition obtained in Example 1-2 in a 35-mL glass bottle, adding 3.3 g of dipropylene glycol monobutyl ether (BuDPG), stoppering the glass bottle, and shaking the contents thoroughly.

<Example 2-1> Surfactant for Flexible Foams

A 500-mL reaction vessel was charged with 50.6 g of a SiH group-containing organopolysiloxane represented by an average composition formula of $MD_{78}D^H_{5.0}M$, 153.4 g of a one-ended allyl polyether represented by an average composition formula of $CH_2=CH-CH_2-O(C_2H_4O)_{22}(C_3H_6O)_{22}-H$, and 34 g of dipropylene glycol monobutyl ether (BuDPG), and the temperature was raised to 90° C. while stirring the contents under a nitrogen flow. The allyl/SiH mass ratio in the hydrosilylation reaction was 1.64. Once 2.0 g of a BuDPG solution of platinum-2,4,6,8-tetramethyl-2,4,6,8-tetravinyl tetrasiloxane complex (Pt concentration: 0.02 wt %) had been added, the reaction solution was clear within an hour. The reaction was conducted for a total of 3 hours. Next, 1 g of reaction solution was collected and completion of the reaction was verified using the alkali decomposition gas generation method.

In this way, a polyether-modified silicone composition was obtained in the form of a liquid in which the ratio of polyether-modified silicone represented by an average composition formula $MD_{78}D^*_{5.0}M$ {where, $*=-C_3H_6O(C_2H_4O)_{22}(C_3H_6O)_{22}-H$} to unreacted polyether to BuDPG was 60:25:15. Here, the polyether moiety was a random adduct of ethylene oxide and propylene oxide.

<Example 3-1> Surfactant for Flexible Foams

A 500-mL reaction vessel was charged with 50.6 g of a SiH group-containing organopolysiloxane represented by an average composition formula of $MD_{78}D^H_{5.0}M$, 65.4 g of a one-ended allyl polyether represented by an average composition formula of $CH_2=CH-CH_2-O(C_2H_4O)_{12}(C_3H_6O)_{16}-CH_3$, 65.3 g of a one-ended allyl polyether represented by an average composition formula of $CH_2=CH-CH_2-O(C_2H_4O)_{25}(C_3H_6O)_{37}-CH_3$, and 58 g of dipropylene glycol monobutyl ether (BuDPG), and the temperature was raised to 90° C. while stirring the contents under a nitrogen flow. The allyl/SiH mass ratio in the hydrosilylation reaction was 1.58. Once 2.0 g of a BuDPG solution of platinum-2,4,6,8-tetramethyl-2,4,6,8-tetravinyl tetrasiloxane complex (Pt concentration: 0.01 wt %) had been added, the reaction solution was clear within an hour. The reaction was conducted for a total of 3 hours. Next, 1 g of reaction solution was collected and completion of the reaction was verified using the alkali decomposition gas generation method.

In this way, a polyether-modified silicone composition was obtained in the form of a liquid in which the ratio of polyether-modified silicone represented by an average composition formula $MD_{78}D^*_{3.4}D^{**}_{1.6}M$ {where, $*=-C_3H_6O(C_2H_4O)_{12}(C_3H_6O)_{16}-CH_3$} to unreacted polyether to BuDPG was 55:20:25. Here, the polyether moiety was a random adduct of ethylene oxide and propylene oxide.

<Example 4-1> Surfactant for Flexible Foams

A 500-mL reaction vessel was charged with 48.0 g of a SiH group-containing organopolysiloxane represented by an average composition formula of $MD_{171}D^H_{19}M$, 6.7 g of a one-ended allyl polyether (1) represented by an average composition formula of $CH_2=CH-CH_2-O(C_2H_4O)_{12}-H$, 78.9 g of a one-ended allyl polyether (2) represented by an average composition formula of $CH_2=CH-CH_2-O(C_2H_4O)_{12}(C_3H_6O)_{16}-(CO)CH_3$, 78.9 g of a one-ended allyl polyether (3) represented by an average composition formula of $CH_2=CH-CH_2-O(C_2H_4O)_{25}(C_3H_6O)_{37}-(CO)CH_3$, and 37.5 g of dipropylene glycol monobutyl ether (BuDPG), and the temperature was raised to 95° C. while stirring the contents under a nitrogen flow. The allyl/SiH mass ratio in the hydrosilylation reaction was 1.31. Once 9 μL (corresponding to 0.01 g) of a platinum-2,4,6,8-tetramethyl-2,4,6,8-tetravinyl tetrasiloxane complex catalyst solution (Pt concentration: 24.7 wt %) had been added, the reaction solution was semi-clear within 10 minutes. After aging for 2.5 hours, 1 g of reaction solution was collected and completion of the reaction was verified using the alkali decomposition gas generation method. It was found that the conversion rate was 75% and that the reaction was not yet complete. After raising the temperature to 125° C. and aging the solution for another 2 hours, the solution had become a clear liquid, and the conversion rate had reached 90%. In order to complete the reaction, 25 g of BuDPG and 14.4 g each of allyl polyethers (2) and (3) were added to the reaction system, 9 μL (equivalent to 0.01 g) of the catalyst solution was added, and the reaction was continued for 5 hours at 125° C. As a result, the reaction was completed. The final allyl/SiH mass ratio was 1.52. The liquid was a brown transparent liquid, and it was found that only a slight amount of brown platinum catalyst aggregate (gel-like) was attached to the stirring rod.

After filtration, a polyether-modified silicone composition was obtained in the form of a clear, homogeneous liquid in which the ratio of polyether-modified silicone represented by an average composition formula $MD_{171}D*_{10.9}D_{5.1}D*_{3}M$ {where, $*=-C_3H_6O(C_2H_4O)_{12}(C_3H_6O)_{16}-(CO)CH_3$, $**=-C_3H_6O(C_2H_4O)_{25}(C_3H_6O)_{37}-(CO)CH_3$, $=-C_3H_6O(C_2H_4O)_{12}-H$} to unreacted polyether to BuDPG was 49.3:25.7:25. Here, the polyether moiety was a random adduct of ethylene oxide and propylene oxide.

<Comparative Example 1-1> Surfactant Usable in Both Rigid and Flexible Foams

A 500-mL reaction vessel was charged with 43.50 g of a SiH group-containing organopolysiloxane represented by an average composition formula of $MD_{43.3}D^H_{6.7}M$, 183.09 g of a one-ended allyl polyether represented by an average composition formula of $CH_2=CH-CH_2-O(C_2H_4O)_{24}(C_3H_6O)_6-CH_3$, and 44.3 g of toluene, and the temperature was raised to 75° C. while stirring the contents under a nitrogen flow. The allyl/SiH mass ratio in the hydrosilylation reaction was 1.567. Then, 200 ppm of a 5% IPA solution of chloroplatinic acid (Pt concentration: 1.9 wt %) was added, and the reaction was conducted for 2 hours. Next, 1 g of reaction solution was collected and completion of the reaction was verified using the alkali decomposition gas generation method. After neutralization with 550 ppm of sodium bicarbonate, the reaction system was heated to 125° C. while gradually reducing the pressure in order to gradually distill off the toluene while watching out for bumping. After stopping distillation of toluene and maintaining the reaction system at 40 hPa or less for one hour, the reaction system was cooled to 70° C., and repressurized. Next, 28.9 g of the one-end allyl polyether was added (for dilution) and the mixture was homogenized. Solid-liquid separation was then performed by filtration using diatomaceous earth.

In this way, a polyether-modified silicone composition was obtained in the form of a liquid in which the ratio of polyether-modified silicone represented by an average composition formula $MD_{43.3}D*_{6.7}M$ {where, $*=-C_3H_6O(C_2H_4O)_{24}(C_3H_6O)_6-CH_3$} to unreacted polyether was 62.8:37.2. Here, the polyether moiety was a random adduct of ethylene oxide and propylene oxide. (Yield: 230 g)

<Comparative Example 1-2>

A 500-mL reaction vessel was charged with 49.0 g of a SiH group-containing organopolysiloxane represented by an average composition formula of $MD_{43.3}D^H_{6.7}M$, 206.0 g of a one-ended allyl polyether represented by an average composition formula of $CH_2=CH-CH_2-O(C_2H_4O)_{24}(C_3H_6O)_6-CH_3$, and 45 g of diethylene glycol monobutyl ether (BuDEG), and the temperature was raised to 80° C. while stirring the contents under a nitrogen flow. The allyl/SiH mass ratio in the hydrosilylation reaction was 1.567. Once 10 μL (corresponding to 0.012 g) of a platinum-2,4,6,8-tetramethyl-2,4,6,8-tetravinyl tetrasiloxane complex catalyst solution (Pt concentration: 24.7 wt %) had been added and heated to 90° C. to 100° C., the reaction solution was almost clear within 40 minutes. The reaction was conducted for a total of 2.5 hours. Next, 1 g of reaction solution was collected and completion of the reaction was verified using the alkali decomposition gas generation method. However, it was found that a considerable amount (approx. 1-2 cm³ by volume) of brown platinum catalyst aggregate (gel-like) was attached to the stirring rod, and some gel particles were suspended in the liquid.

After filtration, a polyether-modified silicone composition was obtained in the form of a liquid in which the ratio of polyether-modified silicone represented by an average composition formula $MD_{43.3}D*_{6.7}M$ {where, $*=-C_3H_6O(C_2H_4O)_{24}(C_3H_6O)_6-CH_3$} to unreacted polyether to BuDEG was 60:25:15. Here, the polyether moiety was a random adduct of ethylene oxide and propylene oxide.

<Comparative Example 1-3>

A 500-mL reaction vessel was charged with 49.0 g of a SiH group-containing organopolysiloxane represented by an average composition formula of $MD_{43.3}D^H_{6.7}M$, 206.0 g of a one-ended allyl polyether represented by an average composition formula of $CH_2=CH-CH_2-O(C_2H_4O)_{24}(C_3H_6O)_6-CH_3$, and 45 g of polypropylene glycol monobutyl ether (BuPPG) represented by an average composition formula of $C_4H_9-O(C_3H_6O)_{11}H$, and the temperature was raised to 100° C. while stirring the contents under a nitrogen flow. The allyl/SiH mass ratio in the hydrosilylation reaction was 1.567. Once 10 μL (corresponding to 0.012 g) of a platinum-2,4,6,8-tetramethyl-2,4,6,8-tetravinyl tetrasiloxane complex catalyst solution (Pt concentration: 24.7 wt %) had been added, the reaction solution was almost clear within 1.5 hours. The reaction was conducted for a total of 3 hours. Next, 1 g of reaction solution was collected and completion of the reaction was verified using the alkali decomposition gas generation method. However, it was found that a considerable amount (approx. 1-2 cm³ by volume) of brown platinum catalyst aggregate (gel-like) was attached to the stirring rod, and some gel particles were suspended in the liquid.

In this way, a polyether-modified silicone composition was obtained in the form of a liquid in which the ratio of polyether-modified silicone represented by an average composition formula $MD_{43.3}D*_{6.7}M$ {where, $*=-C_3H_6O(C_2H_4O)_{24}(C_3H_6O)_6-CH_3$} to unreacted polyether to BuPPG was 60:25:15. Here, the polyether moiety was a random adduct of ethylene oxide and propylene oxide.

<Comparative Example 4-1> Surfactant for Flexible Foams

A 500-mL reaction vessel was charged with 48.0 g of a SiH group-containing organopolysiloxane represented by an average composition formula of $MD_{171}D^H_{19}M$, 6.7 g of a one-ended allyl polyether (1) represented by an average composition formula of $CH_2=CH-CH_2-O(C_2H_4O)_{12}-H$, 78.9 g of a one-ended allyl polyether (2) represented by an average composition formula of $CH_2=CH-CH_2-O$ $(C_2H_4O)_{12}(C_3H_6O)_{16}$—$(CO)CH_3$, 78.9 g of a one-ended allyl polyether (3) represented by an average composition formula of $CH_2$=$CH$—$CH_2$—$O(C_2H_4O)_{25}(C_3H_6O)_{37}$—$(CO)CH_3$, and 37.5 g of polypropylene glycol monobutyl ether (BuPPG) represented by an average composition formula of $C_4H9$-$O(C_3H_6O)_{11}H$, and the temperature was raised to 100° C. while stirring the contents under a nitrogen flow. The allyl/SiH mass ratio in the hydrosilylation reaction was 1.31. Once 9 μL (corresponding to 0.01 g) of a platinum-2,4,6,8-tetramethyl-2,4,6,8-tetravinyl tetrasiloxane complex catalyst solution (Pt concentration: 24.7 wt %) had been added, the reaction solution was almost clear within 15 minutes. After aging for 3.5 hours, 1 g of reaction solution was collected and completion of the reaction was verified using the alkali decomposition gas generation method. It was found that the conversion rate was 75% and that the reaction was not yet complete. Also, a considerable amount of brown platinum catalyst aggregate (gel-like) was attached to the stirring rod. In order to complete the reaction, 25 g of BuPPG and 14.7 g each of allyl polyethers (2) and (3) were added to the reaction system, 9 μL (equivalent to 0.01 g) of the catalyst solution was added, and aging was conducted for 3 hours at 125° C. However, there was no significant change in the conversion rate. Another 24.6 g each of allyl polyethers (2) and (3) had to be added again to the reaction system. When the situation was observed after one hour, the liquid had gelled and become caked on the stirring rod. At this point, the test was ended.

[Properties of Reaction Solvent or Diluent]

In order to select a suitable solvent for a polyether-modified silicone, the physical properties of many industrial produced candidate compounds are shown in Table 1. In order to take into account use as a foam stabilizer for polyurethane foam and reduce migration from the foam, non-reactive compounds have been excluded. Compounds that solidify at low winter temperatures and compounds with a low flash point have also been excluded. The terminal structure represented by $(C_3H_6O)$—H in the chemical structures of Table 1 may include isomers. However, secondary alcoholic hydroxyl groups represented by $CH_2CH(CH_3)$—OH are usually formed.

Among the solvents listed in Table 1 Nos. RE1 to RE15 are components that do not fall under component (B) of the invention in the present application, but No. 1 to No. 4 are components that fall under component (B) of the invention in the present application. The following is a comparison of the suitability of these components as a solvent for polyether-modified silicone compositions.

Based on the data in Table 1, when branched higher alcohols such as isostearyl alcohol (ISA, RE1), PPG derivatives (RE3, RE4) that are polymer-type diluents, diols (RE5 to RE7), and phenyl glycol derivatives (RE8 to RE10) are used to dilute a highly viscous polyether-modified silicone, the viscosity-reducing effect is not very dramatic. In other words, it is clear that the amount of diluent used has to be increased in order to lower the viscosity of a surfactant composition, and there is a trade-off between efficient surface activity and the isocyanate index.

In addition, ISA has a compatibility problem with high polarity components such as polyols and surfactants, PPG derivatives have an affinity problem with water, and phenyl ether derivatives generally have a high melting point and are too expensive to be used in polyurethane foam production. Texanol (RE2) is good from the standpoint of a relatively low viscosity, but has few structural elements similar to an oxyalkylene group in the molecule. As a result, it has compatibility problems with strongly hydrophilic polyethylene glycol (PEG) homopolymers.

Therefore, in order to improve formulations of polyurethane foam-forming compositions and compatibility with each component, stabilize and improve foam properties, and contribute to the realization of a stable production process for foam, only solvents in the group of compounds known as "glycol ethers" are selected and combined with polyether-modified silicones. These are preferably used as surfactant solutions. From a safety standpoint, the solvent preferably has a flash point of 80° C. or higher, preferably 90° C. or higher.

TABLE 1

Solvent for Polyether-Modified Silicone (Diluent)

| No. | Abbreviation | Chemical Structure* | Visc. [cs] (25° C.) | Freezing Pt. or Pour Pt. [° C.] | Boiling Pt. [° C.] | Flash Pt. [° C.] |
|---|---|---|---|---|---|---|
| RE1 | ISA | $Me_2CH$—$(CH_2)_{15}$—OH | 56 | <−30 | 292-302 | 194 |
| RE2 | TEXANOL | $Me_2CH$—(CO)O—$CH_2CHMe_2$—CH(OH)—$CHMe_2$ | 13.6 | <−50 | 255-260 | 120 |
| RE3 | PPG | $HO(C_3H_6O)_{6.6}$—H | 68 | 45 | NA (Polymer) | 180 |
| RE4 | BuPPG | Butyl-O $(C_3H_6O)_{10.5}$—H | 70 | <−35 | NA (Polymer) | 210 |
| RE5 | PG | HO—$(C_3H_6O)$—H | 47 | <−57 | 187 | 99 |
| RE6 | DPG | HO—$(C_3H_6O)_2$—H | 73 | 39 | 232 | 132 |
| RE7 | TPG | HO—$(C_3H_6O)_3$—H | 56 | 41 | 265 | 141 |
| RE8 | PhEG | Phenyl-O—$(C_2H_4O)$—H | 20.5 | 14 | 245 | 127 |
| RE9 | PhDEG | Phenyl-O—$(C_2H_4O)_2$—H | >20.5 | <−30 | 283 | 160 |
| RE10 | PhPG | Phenyl-O—$(C_3H_6O)$—H | 21.4 | 11 | 241 | 115 |
| RE11 | BuEG | Butyl-O$(C_2H_4O)$—H | 3 | <−70 | 171 | 62 |
| RE12 | BuDEG | Butyl-O$(C_2H_4O)_2$—H | 6 | <−70 | 230 | 107 |
| RE13 | BuTEG | Butyl-O$(C_2H_4O)_3$—H | 8 | 48 | 271 | 156 |
| RE14 | MeDPG | Me—O$(C_3H_6O)_2$—H | 3.8 | −80 | 190 | 79 |
| RE15 | BuPG | Butyl-O$(C_3H_6O)$—H | 3.3 | −80 | 170 | 62 |
| 1 | MeTPG | Me—O$(C_3H_6O)_3$—H | 5.5 | −80 | 242 | 122 |
| 2 | BuDPG | Butyl-O$(C_3H_6O)_2$—H | 4.9 | <−60 | 229 | 106 |
| 3 | BuTPG | Butyl-O$(C_3H_6O)_3$—H | 7.3 | <−75 | 274 | 138 |
| 4 | PrDPG | Propyl-O$(C_3H_6O)_2$—H | 4.3 | <−60 | 212 | 94 |

*Phenyl = $C_6H_5$, Butyl = $C_4H_9$, Propyl = $C_3H_7$, Me = $CH_3$

Also, there is growing market demand for polyurethane foams with "low emission" properties. This is expressed as demand for low volatile organic compounds (low VOC) which have fewer volatile components, low emission compounds (which have fewer chemical substances released from the foam), and low fogging compounds (which reduce adhesion of components volatilized from foam used in car interiors from adhering to window glass). The meaning of these terms is essentially the same. Therefore, the solvent is preferably expected to become incorporated into the polyurethane backbone chain, and essentially be non-volatile (equal to having a boiling point of 200° C. or higher). Based on this study, among the compounds listed in Table 1, the solvents that can suitably be used in a polyether-modified silicone composition are No. 1 to No. 4, RE12, and RE13. In other words, the other solvent compounds are not preferred because they include an inappropriate physical property. As described below, RE12 and RE12, which do not include secondary alcoholic hydroxyl groups (but rather primary alcoholic hydroxyl groups) perform poorly compared to the invention of the present application when used as solvents for polyether-modified silicone compositions, especially synthesis solvents, in terms of reproducibility and side reaction risk due to variations in raw material lots (such as in acidic impurities), composition usefulness, and production efficiency.

[Properties of Compositions in the Examples and Comparative Examples]

The design structures, details, appearance, and viscosity at 25° C. ($mm^2/s$) of the resulting compositions in Examples 1-1 to 1-2, Examples 2-1 to 4-1, and Comparative Examples 1-1 to 1-3 are shown in Table 1 and Table 2 below.

TABLE 2

Design Structure and Content of Each Material Obtained in the Examples

| Example | | Properties of Composition | | Structure of Polyether-Modified Silicone (A) | | | | Solvent | (A)/(B) |
|---|---|---|---|---|---|---|---|---|---|
| No. | Reactivity | Appearance | Visc. | m | n | t1/t2 | Y | (B) | mass ratio |
| 1-1 | Good | Clear Uniform | 750 | 6.7 | 43.3 | 24/6 | Me | BuDPG | 93/7 |
| 1-2 | Good | Clear Uniform | 369 | 6.7 | 43.3 | 24/6 | Me | BuDPG | 80/20 |
| 1-3 | — | Clear Uniform | 216 | 6.7 | 43.3 | 24/6 | Me | BuDPG | 68/32 |
| 2-1 | Good | Clear | No data | 5.0 | 78 | 22/22 | H | BUDPG | 80/20 |
| 3-1 | Good | Clear | No data | 5.0 | 78 | 12/16 & 25/37 | Me & Me | BuDPG | 69/31 |
| 4-1 | Bit Low | Somewhat Clear* | 23,770 | 19 | 171 | 12/0 & 12/16 & 25/37 | H & COCH3 & COCH3 | BuDPG | 66/34 |

Note
*A slight amount of catalyst aggregate (gel) adhered to the stirrer before filtration (after the reaction).

TABLE 3

Design Structure and Content of Each Material Obtained in the Comparative Examples

| Comp. Example | | Properties of Composition | | Structure of Polyether-Modified Silicone (A) | | | | Solvent | (A)/(b) |
|---|---|---|---|---|---|---|---|---|---|
| No. | Reactivity | Appearance | Visc. | m | n | t1/t2 | Y | (b) | mass ratio |
| 1-1 | Good | Clear Uniform | 764 | 6.7 | 43.3 | 24/6 | Me | None | — |
| 1-2 | Good | Generally Clear* | 405 | 6.7 | 43.3 | 24/6 | Me | BuDEG | 80/20 |
| 1-3 | Good | Generally Clear* | 571 | 6.7 | 43.3 | 24/6 | Me | BuPPG | 80/20 |
| 4-1 | Poor | Gel | Unmeasurable | 19 | 171 | 12/0 & 12/16 & 25/37 | H & COCH3 & COCH3 | BuPPG | 66/34 |

Note
*A considerable amount of catalyst aggregate (gel) adhered to the stirrer before filtration (after the reaction).

In Comparative Example 1-3 and Comparative Example 4-1, an attempt was made to use polyglycols (BuPPG) commonly used as diluents in polyether-modified silicones as the synthesis solvent for the copolymers. In the case of the former where the molecular weight of the modified silicone was not so high, the hydrosilylation in the main reaction proceeded well and the desired product was obtained. However, in the case of the latter where the molecular weight of the modified silicone was somewhat high, the main reaction proceeded very slowly and was never completed because the entire reaction system gelled up. The cause was the high molecular weight of polyglycols, their inability to compatibilize a SiH group-containing organopolysiloxane and terminal alkenyl group-containing polyether, and their ineffectiveness at lowering the viscosity of the reaction system to increase opportunities for contact and mixing. Therefore, the visible gel structure of the entire reaction solution is thought to be the result of a non-negligible side reaction that causes crosslinking as the main reaction becomes stagnant. Also, in the case of Comparative Example 1-3, where the molecular weight of the modified silicone is not that high, a significant amount of catalyst aggregate (gel) adhered to the stirring rod unlike Example 1-1 and Example 1-2. This is because the compatibility between polyglycols BuPPG and the catalyst is insufficient, and because it does not effectively dissolve and disperse the catalyst throughout the entire reaction system. Because polyglycols are generally not recognized or used as reaction solvents for modified silicones and alkali catalysts are often used in the manufacturing process, manufacturers of the raw materials have not recognized the need to remove all traces of residual alkalis from each production batch. Therefore, when such a raw material is used as a solvent in the hydrosilylation reaction, the reaction is greatly affected by fluctuations in the impurity levels in each production lot of the raw material (alkalis can stop reactions by deactivating platinum catalysts, etc.), which makes stable production of modified silicones impossible on an industrial scale. Also, because polyglycols have several ether bonds in the molecule, they readily oxidized in contact with air to form peroxides. Because peroxides also interrupt the hydrosilylation catalytic cycle by deactivating the platinum catalysts, there are significant industrial disadvantages when general polyglycols are used as a hydrosilylation reaction solvent.

In Comparative Example 1-1, the hydrosilylation reaction proceeded well and produced a polyether-modified silicone. However, toluene is toxic, flammable, hydrophobic and cannot produce a composition of the present invention unless solvent substitution occurs.

In Comparative Example 1-2, diethylene glycol monobutyl ether (BuDEG) which does not fall under component (B) of the present invention was used as a solvent. Although the hydrosilylation in main reaction proceeded well and the desired product was obtained, a considerable amount of catalyst aggregate (gel) adhered to the stirring rod. This is thought to be due to the lack of compatibility of BuDEG with the catalyst, which could not effectively dissolve and disperse the catalyst throughout the reaction system. Furthermore, BuDEG is a hazardous air pollutant that falls under the Hazardous Air Pollutants Act, and is regulated in the United States. As a result, industrial use is greatly restricted compared to the BuDPG used in the examples due to safety and environmental concerns.

Glycol ethers with low molecular weights and a small number of repeating units have been considered "glycol ethers" because of their relatively similar structures and properties. However, as a result of extensive research on these compounds as reaction solvents and residual diluents in polyether-modified silicones, a considerable difference in usefulness has been discovered in the case of glycol ether EO derivatives having no secondary alcoholic hydroxyl group and glycol ether PO derivatives having secondary alcoholic hydroxyl groups. In Example 1-2, no gel was observed in the solution after completion of the reaction. However, in Comparative Example 1-2, a considerable amount of catalyst aggregate (gel) was found to be adhering to the stirring rod by the end of the reaction. During industrial production, catalyst aggregates such as these clogging filters during filtration and building up in reaction vessels often cause significant decline in production efficiency. Even the small amounts observed in the laboratory have an undesirable effect on industrial production. Also, the reactivity of the hydroxyl group is high in BuDEG, which has a primary alcoholic hydroxyl group. Therefore, when trace amounts of acidic impurities from raw materials are present in the reaction system, the hydroxyl group is believed to have an increased likelihood of competitively reacting with and blocking the reaction point of the SiH group-containing organopolysiloxane. There is also a higher risk of obtaining polyether-modified silicones with a lower molecular weight (fewer polyether pendant chains attached to the polysiloxane backbone) than called for in the design of the hydrosilylation reaction. Because of these concerns, Table 4 shows a comparison of GPC analysis results from Comparative Examples 1-1 to 1-3, Examples 1-1, and Example 1-2. During this analysis, filtered samples from the synthesis testing performed on the comparative examples were subjected to GPC because of the production of gel.

The following were the measurement conditions in the GPC analysis.

<GPC Measurement Conditions>
Eluent: Chloroform (reagent grade)
Measurement Temperature: 40° C.
Detector: Refractometer (peak detection on positive side)
Flow rate: 1.0 mL/min
Calibration: Performed with standard polystyrene
Sample solution injection volume: 100 μL (sample concentration 1 wt %)

TABLE 4

Relationship Between Alcoholic Hydroxyl Group Properties and Polyether-Modified Silicone GPC Data

| Sample | Diluent (After Added) | Alcoholic Properties of Diluent | No. Avg. Mol. Wt. of Copolymer | Peak Area Ratio % of Unreacted Polyether to Copolymer | SiOC Signal Intensity ($^{29}$Si-NMR) |
|---|---|---|---|---|---|
| C. Ex. 1-1 | Raw Polyester | None | 23,700 | 175 | ND (Not Detected) |
| Ex. 1-1 | BuDPG | Secondary | 23,000 | 115 | ND (Not Detected) |
| Ex. 1-2 | BuDPG | Secondary | 23,600 | 122 | ND (Not Detected) |
| C. Ex. 1-2 | BuDEG | Primary | 23,500 | 130 | ND (Not Detected) |
| C. Ex. 1-3 | BuPPG | Secondary | 23,700 | 149* | ND (Not Detected) |

Note
*BuPPG diluent peaks overlap with unreacted polyether peaks and are counted in the calculations.

In the case of the relatively high molecular weight polyether-modified silicone samples, the target polyether-modified silicones (copolymers) are believed to be obtained normally based on GPC and $^{29}$Si NMR. However, when the GPC of Comparative Example 1-2, which uses BuDEG having a primary alcoholic hydroxyl group as the reaction solvent, is compared to the GPC of Example 1-1 and Example 1-2, which use BuDPG having a secondary alcoholic hydroxyl group as the reaction solvent, it is clear that a larger amount of unreacted polyether remains in the copolymer in the comparative example. Therefore, while it cannot be detected at current levels of $^{29}$Si NMR sensitivity, it is believed that, in those portions of Comparative Example 1-2 without an allyl polyether to react with as intended (quantitatively, the probability for BuDEG is high), the Si—H group in the raw material polysiloxane was consumed by a dehydrogenation reaction.

Specifically, it is believed that glycol ethers having a low molecular weight and a small number of repeating units and in which the terminal hydroxyl group is a secondary alcoholic hydroxyl group do not participate in the aforementioned competitive reaction, the hydrosilylation reaction of the organic hydrogen polysiloxane and the allyl group-containing polyether starting materials proceeds selectively as designed, and produce a polyether-modified silicone having a single molecular weight distribution and a molecular weight close to that of the designed structure.

It is clear from Table 2 and Table 4 that a polyether-modified silicone having a single molecular weight distribution and high utility close to that of the designed structure can be obtained by using a monool organic compound serving as component (B) of the present invention. Also, component (B) of the invention in the present application has a much better viscosity-reducing effect on polyether-modified silicone compositions (contributing to improved handling, production efficiency, and reactivity) than the diluents in the comparative examples. The reaction solvent and residual diluent for a polyether-modified silicone in the present invention is component (B) in the present invention, which is a specific type of glycol ether compound that is liquid at 5° C., that has one secondary alcoholic hydroxyl group in the molecule, and that does not contain any heteroatom other than oxygen. Other such cases have not been reported within the scope researched by the present inventors.

Because glycol ethers having a low molecular weight and a small number of repeating units serving as component (B) are available in the market in distilled and purified form, they do not impede hydrosilylation due to impurities, they can easily compatibilize a SiH group-containing organopolysiloxane and a polyether with an alkenyl group on one end from the standpoint of molecular structure, and they can be used as reaction solvents and diluents to obtain a polyether-modified silicone composition having a singular primary component molecular weight distribution while minimizing side reactions.

[Properties of Compositions in the Examples and Comparative Examples: Hydrogel-Forming Properties]

Next, the present inventors tested the ability of compositions of the present invention to solve the problem usage restrictions due to the tendency of polyether-modified silicones to thicken or form a hydrogel in the presence of water. This problem affects, for example, urethane foam formulations in which the open cell rate is to be adjusted or in which open cells are desired, cases in which the storage stability of a premix solution has to be good, and cases in which some components are blended together beforehand and sold as a formula system. Here, Examples 1-1 and 1-2 served as polyether-modified silicone compositions of the present invention, Comparative Examples 1-1 and 1-3 served as polyether-modified silicone compositions of the prior art, and a water miscibility test was conducted on the examples and on the comparative examples. The following was the testing method.

<Testing Method>

A 200-mL glass bottle was charged with 40 g of a polyether-modified silicone composition and 20 g of water, and the contents were mixed for 5 minutes at room temperature using a Homo Disper mixer set to 1,600 rpm. The properties of the resulting mixture were observed and recorded immediately after preparation and after standing at room temperature for a day. The results are shown in Table 5 below.

TABLE 5

Results of Water Miscibility Test

| Sample | Component (A) % | Unreacted Polyether % | Diluent (B) or (b) % | Water % | Properties Right After Preparation | Properties After 1 Day |
|---|---|---|---|---|---|---|
| C. Ex. 1-1 | 42% | 25% | NA | 33% | Clear Viscous Liquid | Same as Left |
| Ex. 1-1 | 45% | 19% | BuDPG 3% | 33% | Clear Viscous Liquid | Same as Left |
| Ex. 1-2 | 40% | 17% | BuDPG 10% | 33% | Clear Low-Viscosity Liquid | Same as Left |
| C. Ex. 1-3 | 40% | 17% | BuPPG 10% | 33% | Cloudy Viscous Liquid | Same as Left |

It was clear from these results that a polyether-modified silicone composition of the present invention is less likely to experience thickening or hydrogel formation due to contact with water than a polyether-modified silicone composition of the prior art even when the concentration of modified silicone is higher, and the problems described above are effectively eliminated by increasing the amount of the component (B). It is also clear that formation of a composition using both a polyether-modified silicone (A) and component (B) of the present invention is key to solving these problems. Meanwhile, it is clear from the results of the water miscibility test on Comparative Example 1-3 that a polyether-modified silicone composition using BuPPG as the diluent has poor compatibility with water, becomes cloudy, and has no effect on suppressing thickening due to hydrogel formation.

As mentioned above, a polyether-modified silicone composition of the present invention can be used in urethane foam formulations in which the open cell rate is to be adjusted or in which open cells are desired, cases in which the storage stability of a premix solution has to be good, and cases in which some components are blended together beforehand and sold as a formula system, whether they be rigid, flexible, or HR applications.

[Low-Temperature Stability of Examples and Comparative Examples]

About 28 g to 29 g of each composition in the examples and comparative examples were weighed out in a 35-mL glass bottle and stoppered, the glass bottles were stored for two hours in an explosion-proof refrigerator set to an internal temperature of 1° C., and the appearance of each composition was observed and recorded at a constant temperature. The results are shown in the following Table.

TABLE 6

| Sample | Type of Diluent (After Added) | Amt. of Diluent in Composition (mass %) | Appearance (25° C.) | Appearance (1° C.) |
|---|---|---|---|---|
| C. Ex. 1-1 | Raw Polyether | 11.3 | Slightly/Semi-Clear Liquid | Cloudy Liquid |
| C. Ex. 1-2 | BuDEG | 15 | Clear Homogeneous Liquid | Cloudy Liquid |
| C. Ex. 1-3 | BuPPG | 15 | Clear Homogeneous Liquid | Cloudy Liquid |
| Ex. 1-1 | BuDPG | 5 | Clear Homogeneous Liquid | Cloudy Liquid |
| Ex. 1-2 | BuDPG | 15 | Clear Homogeneous Liquid | Cloudy Liquid |
| Ex. 1-3 | BuDPG | 25 | Clear Homogeneous Liquid | Clear Homogeneous Liquid |
| Ex. 4-1 | BuDPG | 25 | Clear Homogeneous Liquid | Clear Homogeneous Liquid |

It is clear from the comparative results of Comparative Examples 1-1 to 1-3 and Examples 1-1 to 1-2 for appearance at 25° C./1° C. that polyether-modified silicone compositions having a raw material EO/PO ratio (mass ratio) of 75/25 in the reaction and a long polyether chain became cloudy at low temperatures, but that increasing the amount of BuDPG serving as the diluent in the present invention to 25% dramatically improved low temperature stability and remained clear and homogeneous at 25° C. Example 4-1 used a monoallyl etherified PEG-12 homopolymer believed to cause cloudiness in modified silicone compositions as a raw material polyether for the reaction but contained 25% of the BuDPG diluent of the present invention, and so had excellent low-temperature stability and remained clear and homogeneous at 25° C.

[Polyurethane Foam Formulation and Testing Results for Compositions in the Examples and Comparative Examples]

The present inventors used samples taken from the examples and comparative examples in a rigid urethane foam formulation based on findings related to the different types of polyurethane foam and the molecular weights of compatible polyether-modified silicones, and conducted a foaming test. Examples 1-1 and 1-2, which are polyether-modified silicone compositions (samples) of the present invention that do not have very high molecular weights, were selected and compared to Comparative Example 1-1, which is a polyether-polysiloxane copolymer composition of the prior art prepared using a reaction in toluene.

<Testing Method>

The rigid foam formulations that were tested are shown in Table 7 below. The amount of surfactant added (parts by mass) was changed in three stages, the compositions were foamed, and the appearance of the resulting foam was observed.

TABLE 7

| | Rigid Polyurethane Foam-Forming Composition | | | |
|---|---|---|---|---|
| | Component Name | Details | Parts Added | Mass % |
| Premix Components | Polyol | Sorbitol-Based Polyether Polyol (Hydroxyl Value 450) | 100 | 32.62 |
| | Tert. Amine Catalyst | $Me_2N$—$(CH_2)_6$—$NMe_2$ | 1.8 | 0.59 |
| | Water | (Foaming Agent) * | 6.0 | 1.96 |
| | Polyether-Modified Silicone Composition | Surfactant Composition | or 0.7 or 0.4 | 0.33 or 0.23 or 0.13 |

TABLE 7-continued

| Rigid Polyurethane Foam-Forming Composition | | | |
|---|---|---|---|
| Component Name | Details | Parts Added | Mass % |
| Isocyanate | Polymethylene Polyphenyl Polyisocyanate (Index 110, NCO % = 31.5) | 197.8 | 64.50 |
| Total | | 306.6 ** | 100.00 ** |

\* Carbon dioxide gas is produced by the reaction with the isocyanate.
\*\* The total when the number of parts of surfactant is 1.0.

[Formation of Flexible Polyurethane Foam]

A polyurethane foam-forming composition of the present invention was prepared on a scale so that the total amount in Table 6 was 16.7%, and a polyurethane foam was formed. These operations were carried out in a temperature-controlled room at about 25° C., and all of the raw materials were used after this constant temperature state was reached.

<Testing Method>

The polyol, water, catalyst, and surfactant were accurately weighed out in a 200-mL polycup and stirred at 3,500 rpm for 15 seconds using a disc blade-type disperser mixer. The isocyanate was then added to this premix and the contents were mixed for 7 seconds at 3,500 rpm using the same type of blade. The uniformly mixed urethane foam-forming composition was poured into a 1-L paper cup over 8 seconds and then allowed to foam freely. Next, the foam was left standing for 40 to 60 minutes in the temperature-controlled room. After two hours, the foam was cut in half from the top, and the foam height and cross-sectional cell structure were observed and recorded.

TABLE 8

| | Evaluation Results for Rigid Polyurethane Foam | | | | | |
|---|---|---|---|---|---|---|
| | Activator 1.0 parts | | Activator 0.7 parts | | Activator 0.4 parts | |
| Type of Surfactant | Foam Height | Cell Structure | Foam Height | Cell Structure | Foam Height | Cell Structure |
| C. Ex. 1-1 | Standard | Fine | Standard | Fine | Standard | Coarse |
| Ex. 1-1 | Equal to Standard | Fine | Somewhat Higher than Standard | Fine | Somewhat Higher than Standard | Bit Coarse |
| Ex. 1-2 | Equal to Standard | Fine | Somewhat Higher than Standard | Fine | Somewhat Higher than Standard | Bit Coarse |

It is clear from the results that a rigid polyurethane foam using a polyether-modified silicone composition containing solvent component (B) of the present invention had a rigid polyurethane foam cell structure and foam height equal to or better than the composition in Comparative Example 1-1 using toluene as the solvent, confirming the excellent effect and usefulness of a polyether-modified silicone composition of the present invention as a cell stabilizer or surfactant.

The following are formulation examples of polyurethane foam-forming compositions in which the flexible foam surfactants prepared in Examples 2-1, 3-1, and 4-1 can be used.

TABLE 9

| Flexible Polyurethane Foam-Forming Composition | | | | |
|---|---|---|---|---|
| | Component Name | Details | Parts Added | Mass % |
| Premix Components | Polyol | Glycerin-Based Polyether Polyol (Hydroxyl Value 56) | 100 | 53.95 |
| | Amine Catalyst | NN-dimethylethanol amine/bis (2-dimethyl aminoethyl) ether/ triethylene diamine/ dipropylene glycol = 28/11/11/50 mixture | 0.2 | 0.11 |
| | Water | (Foaming Agent) * | 5.5 | 2.97 |
| | Dichloromethane | $CH_2Cl_2$ | 10.0 | 5.39 |
| | Tin Catalyst | Tin Octoate | 0.27 | 0.15 |

TABLE 9-continued

Flexible Polyurethane Foam-Forming Composition

| Component Name | Details | Parts Added | Mass % |
|---|---|---|---|
| Polyether-Modified Silicone Composition | Surfactant Composition e.g.) Ex. 2-1 or Ex. 3-1 or Ex. 4-1 | 0.8 | 0.43 |
| Isocyanate | Tolylene diisocyanate (Index 110) | 68.6 | 37.00 |
| Total | | 185.37 | 100.00 |

* Carbon dioxide gas is produced by the reaction with the isocyanate.

TABLE 10

Flexible Polyurethane Foam-Forming Composition

| | Component Name | Details | Parts Added | Mass % |
|---|---|---|---|---|
| Premix Components | Polyol | Glycerin-Based Polyester Polyol (Hydroxyl Value 56) | 100 | 59.70 |
| | Amine Catalyst | Triethylene diamine/ dipropylene glycol = 33/67 mixture | 0.2 | 0.12 |
| | | N-ethyl morpholine | 0.1 | 0.06 |
| | Water | (Foaming Agent) * | 3.3 | 1.97 |
| | Dichloromethane | $CH_2Cl_2$ | 20.0 | 11.94 |
| | Tin Catalyst | Tin Octoate | 0.6 | 0.36 |
| | Polyether-Modified Silicone Composition | Surfactant Composition e.g.) Ex. 2-1 or Ex. 3-1 or Ex. 4-1 | 0.6 | 0.36 |
| | Isocyanate | Tolylene diisocyanate (Index 105) | 42.7 | 25.49 |
| | Total | | 167.50 | 100.00 |

* Carbon dioxide gas is produced by the reaction with the isocyanate.

The invention claimed is:

1. A method for manufacturing a polyether-modified silicone composition comprising:
(A) at least one polyether-modified silicone represented by the general Formula (1) below:

$$R_aQ_bSiO_{(4-a-b)/2} \quad (1)$$

where each R independently represents a monovalent hydrocarbon group having 1 to 30 carbon atoms and no aliphatic unsaturated bond or a silicon atom-containing organic group, each Q independently represents a polyoxyalkylene group-containing organic group represented by the general formula: —$C_xH_{2x}$O—$(C_2H_4O)_{t1}(C_3H_6O)_{t2}(C_4H_8O)_{t3}$—Y where x, t1, t2 and t3 are numbers satisfying 2≤x≤8, 0≤t1≤60, 0≤t2≤50, 0≤t3≤50, and 2≤(0+t2+t3)≤110, and Y is selected from a hydrogen atom, alkyl groups having from 1 to 4 carbon atoms, and a $COCH_3$ group, and a and b are numbers in the ranges 1.0≤a≤2.5 and 0.0001≤b≤1.5;
(B) at least one monool organic compound selected from (B1) and/or (B2) below and being a liquid at 5° C. and having one secondary alcoholic hydroxyl group but no heteroatom other than oxygen in the molecule:
(B1) a glycol ether compound having a hydrogen atom substituted by an alkyl group having from 2 to 8 carbon atoms at one end, a secondary alcoholic hydroxy group at the other end, and from 2 to 3 repeating oxyalkylene units having from 2 to 4 carbon atoms,
(B2) a tripropylene glycol monomethyl ether;

wherein isopropyl alcohol (IPA) does not exceed 1 mass % of the composition; and
wherein the method comprises the steps of:
(I″) initiating and/or promoting a hydrosilylation reaction between an organic hydrogen polysiloxane and a polyether compound having an alkenyl group at one end of the molecular chain in the presence of a volatile organic solvent (B') different from component (B); and
(II') conducting solvent exchange of the volatile organic solvent (B') with the monool organic compound serving as component (B).

2. The method according to claim 1, wherein component (A) is a linear polyether-modified silicone represented by the general Formula (1') below:

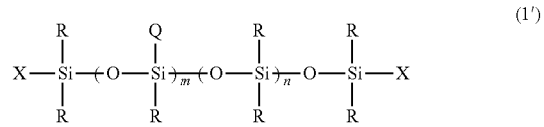

where R and Q are each as defined above, X is R or Q, n is a number from 0 to 1000, and m is a number in a range from 0 to 200, provided at least one X is Q when m is 0.

3. The method according to claim 2, wherein n and m in Formula (1') are numbers in the range 25≤(m+n)≤230.

4. The method according to claim 1, wherein Q is a polyoxyalkylene group-containing organic group excluding a polyoxyethylene group-containing organic group represented by the general formula: $-C_xH_{2x}O-(C_2H_4O)_{t1}-Y$ where $2 \leq x \leq 8$, $10 \leq t1 \leq 60$, and Y is selected from a hydrogen atom, alkyl groups having from 1 to 4 carbon atoms, and a $COCH_3$ group.

5. The method according to claim 1, wherein component (B1) is selected from a group consisting of dipropylene glycol monobutyl ether, tripropylene glycol monobutyl ether, dipropylene glycol mono (iso) propyl ether, tripropylene glycol mono (iso) propyl ether, dipropylene glycol monoethyl ether, and tripropylene glycol monoethyl ether.

6. The method according to claim 1, wherein the mass ratio of component (A) and component (B) is in a range of from 20/80 to 96/4.

7. The method according to claim 1, wherein $1 \leq t2 \leq 50$, and $6 \leq (t1+t2+t3) \leq 50$.

* * * * *